(12) United States Patent
Cheng et al.

(10) Patent No.: US 9,593,197 B2
(45) Date of Patent: Mar. 14, 2017

(54) TRIGGER-RESPONSIVE CHAIN-SHATTERING POLYMERS

(71) Applicant: THE BOARD OF TRUSTEES OF THE UNIVERSITY OF ILLINOIS, Urbana, IL (US)

(72) Inventors: Jianjun Cheng, Champaign, IL (US); Yanfeng Zhang, Urbana, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 72 days.

(21) Appl. No.: 14/401,010

(22) PCT Filed: May 20, 2013

(86) PCT No.: PCT/US2013/041859
§ 371 (c)(1),
(2) Date: Nov. 13, 2014

(87) PCT Pub. No.: WO2013/173834
PCT Pub. Date: Nov. 21, 2013

(65) Prior Publication Data
US 2015/0141453 A1    May 21, 2015

Related U.S. Application Data

(60) Provisional application No. 61/649,205, filed on May 18, 2012, provisional application No. 61/648,715, filed on May 18, 2012, provisional application No. 61/695,097, filed on Aug. 30, 2012, provisional application No. 61/695,093, filed on Aug. 30, 2012.

(51) Int. Cl.
| | |
|---|---|
| *A61K 47/34* | (2006.01) |
| *A61K 9/51* | (2006.01) |
| *A61K 31/4375* | (2006.01) |
| *C08G 18/73* | (2006.01) |
| *C08G 71/04* | (2006.01) |
| *A61K 9/19* | (2006.01) |
| *C08G 18/38* | (2006.01) |
| *C08G 65/34* | (2006.01) |

(52) U.S. Cl.
CPC .......... *C08G 18/384* (2013.01); *A61K 9/5146* (2013.01); *A61K 31/4375* (2013.01); *A61K 47/34* (2013.01); *C08G 18/73* (2013.01); *C08G 65/34* (2013.01); *C08G 71/04* (2013.01); *A61K 9/19* (2013.01); *C08G 2650/12* (2013.01)

(58) Field of Classification Search
CPC ...... A61K 47/34; C08G 18/384; C08G 71/04; C08G 18/73
See application file for complete search history.

(56) References Cited

U.S. PATENT DOCUMENTS

| | | |
|---|---|---|
| 2005/0271615 A1 | 12/2005 | Shabat |
| 2006/0269480 A1 | 11/2006 | Amir |
| 2007/0009980 A1 | 1/2007 | Graham |

FOREIGN PATENT DOCUMENTS

| | | |
|---|---|---|
| JP | H2-205849 | 8/1997 |
| WO | 2011038117 A2 | 3/2011 |

OTHER PUBLICATIONS

De Groot et al, Angewandte Chemie International Edition, "Cascade-Release Dendrimers" Liberate All End Groups upon a Single Triggering Event in the Dendritic Core, 2003, 42, pp. 4490-4494.*
Zaragoza Dorwald, Side Reactions in Organic Synthesis, 2005, WILEY-VCH Verlag GmbH & Co. KGaA, Weinheim, Preface. p. IX.*
Warnecke et al, Journal of Organic Chemistry, 2,4-Bis(hydroxymethyl) aniline as a Building Block for Oligomers with Self-Eliminating and Multiple Release Properties, 2008, 73, pp. 1546-1552.*
Nakajima et al, STN Abstract XP-002714815, 1991,pp. 1-6.*
Liu et al, Pharmaceutical Science & Technology Today, Designing dendrimers for drug delivery, 1999, 2(10), pp. 393-401.*
Day, M. et al., "Thermal Analysis of Some Environmentally Degradable Polymers" Journal of Thermal Analysis, vol. 52 (1998) 261-274.
De Clercq, Ronny et al., "Polymer Networks Containing Degradable Polyacetal Segments", Macromolecules 1992,25, 1109-1113.
Dewit, Matthew A. et al., "A Reduction Sensitive Cascade Biodegradable Linear Polymer", Journal of Polymer Science: Part A: Polymer Chemistry, vol. 48, 3977-3985 (2010).
Fiore, Vincent et al., "Polyketal microparticles for therapeutic delivery to the lung" Biomaterials 31 (2010) 810-817.
Gopferich, A. et al., "Polyanhydride degradation and erosion" Advanced Drug Delivery Reviews 54 (2002) 911-931.
Jones, Richard "Biomimetic Polymers Tough and Smart" Nature Materials, vol. 3 Apr. 2004 209-210.
Kumar, Neeraj, et al., "Polyanhydrides: an overview" Advanced Drug Delivery Reviews 54 (2002) 889-910.
Kumar, Ashok, et al., "Smart polymers: Physical forms and bioengineering applications" Prog. Polym. Sci. 32 (2007) 1205-1237.
Perry-Feigenbaum, Rotem, "The pyridinone-methide elimination" Org. Biomol. Chem., 2009, 7, 4825-4828.
Warnecke, Andre et al., "2,4-Bis(hydroxymethyl)aniline as a Building Block for Oligomers with Self-Eliminating and Multiple Release Properties" J. Org. Chem. 2008, 73, 1546-1552.
Weinstain, Roy et al., "Self-Immolative Comb-Polymers: Multiple-Release of Side-Reporters by a Single Stimulus Event" Chem. Eur. J. 2008, 14, 6857-6861.

(Continued)

Primary Examiner — Paul A Zucker
(74) Attorney, Agent, or Firm — McDonnell Boehnen Hulbert & Berghoff

(57) ABSTRACT

Disclosed are polymers containing a backbone comprising alternating N-protected hydroxymethylaniline units ("spacer") and linker units.

7 Claims, 8 Drawing Sheets

(56) References Cited

OTHER PUBLICATIONS

Data Base, Caplus, XP-002714815, Japan, 1991.
Data Base, Caplus, XP-002714814, Japan, 1992.
Greene, Theodora W., et al., "Chapter 7: Protection for the Amino Group", Jan. 1, 1991, Protective Groups in Organic Synthesis, NY, 494-653, XP009107134.
International Search Report and Written Opinion for PCT/US2013/041859, dated Nov. 13, 2013.
International Preliminary Report on Patentability for PCT/US2013/041859, dated Nov. 18, 2014.
Nadezda, Fomina et al., "UV and Near-IR Triggered Release from Polymeric Nanoparticles" J. Am. Chem. Soc. 9 vol. 132, No. 28, 2010, 9540-9542.
Nadezda, Fomina et al., "Low Power, Biologically Benign NIR Light Triggers Polymer Disassembly" Macromolecules 2011, 44, 8590-8597.
Zhao, Yue, "Fast Photodegradable Block Copolymer Micelles for Burst Release" Macromolecules, 2011, 44, 437-439.

* cited by examiner

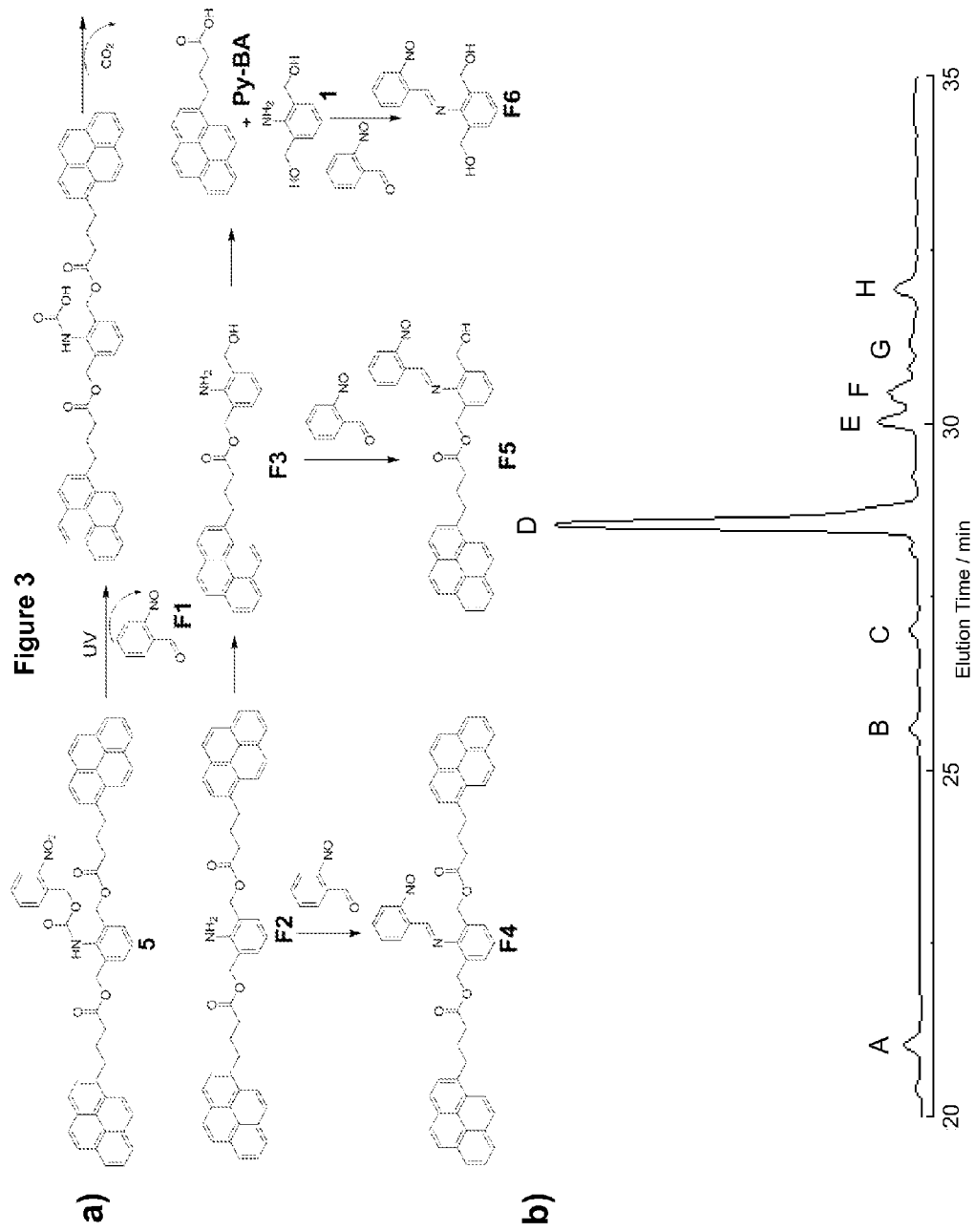

TRIGGER-RESPONSIVE CHAIN-SHATTERING POLYMERS

This application claims priority from International Application No. PCT/US2013/41859, filed, filed May 20, 2013, which claims the benefit of U.S. Provisional Application No. 61/648,715 filed May 18, 2012, U.S. Provisional Application No. 61/649,205 filed May 18, 2012, U.S. Provisional Application No. 61/695,093 filed Aug. 30, 2012, and U.S. Provisional Application No. 61/695,097 filed Aug. 30, 2012. The disclosures of all these applications are herein incorporated by reference in their entirety.

BACKGROUND OF THE INVENTION

Field of the Invention

The invention relates to polymers that can be degraded or depolymerized into component units via a deprotection reaction. More specifically, the invention relates to such polymers that include hydroxymethyl-substituted aniline building blocks. These polymers are functionalized with various protecting groups, which upon deprotection, promote fast degradation of the polymer via a chain-shattering mechanism.

Description of Related Art

Degradable polymers have been known for some time, and initially were sought for long-term biodegradable applications. Recently, polymers that are capable of decomposition under specific conditions have been of interest, and specifically, so called "self-immolative" polymers have received significant attention. Self-immolative polymers are typically composed of a repeating unit that is capped at one end with a functional group which is selectively reactive under specific conditions, i.e. a protecting group. Upon removal of the protecting group, the polymer degrades from one end to the other in a head to tail fashion.

Various approaches to the design, synthesis and de-polymerization of self-immolative polymers have been proposed. Several research groups have reported success with self-immolative polymers that contain repeating hydroxymethylaniline units and a protected terminal amine. When these polymers are subjected to deprotection conditions, the protecting group is removed from the terminal amine and the degradation propagates through the polymer backbone. The key building blocks of these self-immolative polymers are 2- or 4-hydroxymethylanilines, structures that allow the 1,4- or 1,6-elimination necessary for degradation. Although, in some cases, the release of $CO_2$ is the driving force for the degradation of the polymer backbone, the head to tail propagation is a slow process.

Self-immolative oligomers containing an amine-protected 2,4-bis(hydroxymethyl)aniline backbone have also been reported. A major limitation of this system is the necessity for the oligomer to be synthesized in a stepwise fashion; polymerization to obtain long chains of repeating units is not feasible.

A polymer able to immediately degrade in the presence of an external stimuli, thereby releasing repeating units that may comprise chemically or biologically useful compounds would find utility in numerous fields of science and technology.

SUMMARY OF THE INVENTION

It is against the above background that the present invention provides certain advantages and advancements over the prior art.

The disclosed invention relates to polymers containing a backbone that comprises alternating N-protected hydroxymethylaniline units ("spacer") and "linker" units. These spacers are covalently connected to the linkers through the spacer's hydroxyl groups. The linkers are formed from a precursor molecule or reagent ("linking agent") containing at least two functional groups capable of forming a covalent bond with the spacer's hydroxyl groups or that can be converted into groups able to form a chemical bond with the spacer's hydroxyl groups. The pendent amine of the hydroxymethylaniline carries a protecting group. When this protecting group is removed (deprotection), a free amine results, and promotes the degradation of the polymer through successive 1,6 and 1,4 eliminations of each spacer's hydroxymethyl groups. The simultaneous 1,6 and 1,4 eliminations occurring at each repeating spacer unit of the polymer results in a "chain-shattering" depolymerization event, and the immediate degradation of the polymer. The resulting process differs from the stepwise, head to tail propagated degradation of self-immolative polymers.

In one aspect, the invention provides a polymer of Formula I:

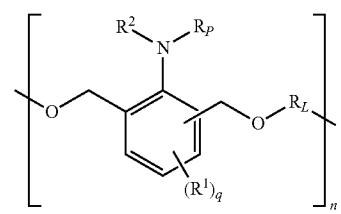

where each $R_P$ is independently a nitrogen protecting group and $R^2$ is a hydrogen, alkyl, alkenyl, alkyl-alkoxy, aryl, or arylalkyl. The —$CH_2O$—$R_L$— substitution occurs at the ortho or para position relative to nitrogen. $R^1$ is independently hydrogen, —$CH_2O$—$R_L$—, alkyl, aryl, alkoxy, arylalkyl, or halogen. When $R^1$ is alkyl, aryl, alkoxy, arylalkyl, or halogen, it may occur at any and all available positions; q can be 1, 2 or 3. When $R^1$ is —$CH_2O$—$R_L$—, however, it occurs at the remaining para or ortho position relative to nitrogen. $R_L$ is a linker, which is covalently bonded to two or more hydroxymethylaniline groups (spacers) in an alternating arrangement that comprises the polymer.

The polymers of Formula I are synthesized through the polymerization of N-protected hydroxymethylaniline (spacer) and a linker containing at least two reactive functionalities. These functionalities include but are not limited to, for example, isocyanates, thioisocyanates, or acid chlorides. Polymerization typically takes place under standard polymerization conditions known in the literature. Depending on the polymerization conditions and the characteristics of the spacer and linker, the resulting polymer can be obtained in the form of an oligomer, dendrimer, cross-linked network, strand, film, layer, fiber, resin, adhesive, coating, hydrogel, organogel, capsule, or particle, such as a nanoparticle, where n is 2 to about 100,000.

The conditions under which the polymer will depolymerize are dependent on the type of nitrogen protecting group incorporated into the polymer backbone. These groups are chosen for their ability to be reactive towards a deprotection agent, i.e. deprotection conditions. The nitrogen protecting group allows the polymer to remain intact under various conditions until the specific deprotection agent is introduced, thereby initiating the depolymerization event. Depolymerization releases the spacer and linker units as individual entities that may be inert or interact with the surrounding environment.

The polymers of the invention can be used to deliver a variety of materials or substances, such as active agents, to a target environment. Representative materials or substances include those that are active (i.e., capable of interacting or reacting with something in their environment), and those that are inactive or inert. Active substances, also referred to herein as active agents, include biologically active agents such as pharmaceuticals and agricultural chemicals, and diagnostic materials such as chromophores and contrast agents, etc. Other materials include acaricides, algaecides, antifeedants, avicides, bactericides, bird repellents, chemosterilants, defoliants, desiccants, disinfectants, fungicides, herbicide safeners, herbicides, insect attractants, insecticides, insect repellents, mammal repellents, mating disrupters, molluscicides, nematicides, plant activators, plant growth regulators, rodenticides, semiochemicals, synergists, and virucides. Still other active agents are those that upon release have chemical reactivity toward, for example, a compound, organism, or other matter in the environment.

The materials and active agents may be encapsulated or contained by the polymer, for example, within particles, films, fibers, or blocks of the polymer. Encapsulation of the substance, e.g., an active agent, may be accomplished either during synthesis of the polymer or in subsequent steps, for example, solution-based encapsulation. In this aspect, the polymer and the material or substance may be in combination as a composition or mixture; the composition or mixture may be in any of various forms, e.g., layer, fiber, particle, coating, or capsule. The invention further comprises method for release of the material or substance from the mixture or composition comprising subjecting the mixture to depolymerization conditions, which include deprotection conditions. The material or substance, e.g., the active agent, is preferably selected such that it will have substantially no depolymerization activity toward the polymer.

Alternatively, the polymer can be synthesized to contain a substance or material, e.g., a biologically active compound or an active agent(s), covalently linked within the polymer molecule so that the substance or material is released upon depolymerization. In this aspect, the substances are capable of being covalently incorporated into the polymer. Preferably the substances have substantially no negative effects on the polymerization reaction.

Polymer materials may also be manufactured according to the invention such that the resulting product will include more than one material or substance, where one or more materials or substances is encapsulated and one or more separate materials or substances is carried in the polymer backbone. Accordingly, the polymer may be manufactured so that the different materials or substances may be released at different times and/or under different conditions.

The invention further provides methods for forming capsules comprising (a) contacting a polymer of the invention with a substance and (b) forming capsules.

These and other features and advantages of the present invention will be more fully understood from the following detailed description of the invention taken together with the accompanying drawings and the claims. It is noted that the scope of the claims is defined by the recitations therein and not by the specific discussion of features and advantages set forth in the present description.

BRIEF DESCRIPTION OF THE DRAWINGS

The following detailed description of certain embodiments of this invention can be best understood when read in conjunction with the following drawings, where like structure is indicated with like reference numerals and in which.

DETAILED DESCRIPTION OF THE INVENTION

Figure 1:
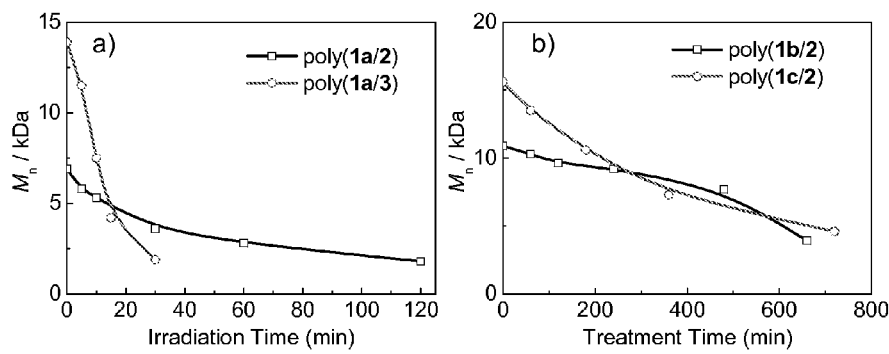
FIG. 1 shows a) the variation of $M_n$ values of poly(1a/2) and poly(1a/3) with duration of UV irradiation; and (b) the variation of $M_n$ values of poly(1b/2) and poly(1c/2) with treatment of 2:1 (v/v) TFA/DCM or piperidine (20% in DMF).

The term "polymer" as used herein, is synonymous with "copolymer", "heteropolymer" and "alternating copolymer" and means a large molecule (macromolecule) composed of a repeating series of two or more alternating monomeric species. These sub-units are typically connected by covalent chemical bonds.

The term "oligomer" as used herein, means a molecule that consists of a few repeating monomer units. An oligomer differs from a polymer in that, at least in principle, a polymer may consist of an unlimited number of monomers. Oligomers include but are not limited to, for example, dimers, trimers, and tetramers.

"Optionally substituted" refers to a group that may be unsubstituted or substituted. For example, "optionally substituted alkyl" means an alkyl group that is either unsubstituted or substituted. A list of optional substituents are listed below in the definition of "substituted."

"Substituted" alkyl, aryl, alkoxyl, and heterocyclyl, refer respectively to alkyl, aryl, alkoxyl, and heterocyclyl, wherein one or more (for example up to about five, in another example, up to about three) hydrogen atoms are replaced by a substituent independently selected from: optionally substituted alkyl (for example, fluoromethyl), optionally substituted aryl (for example, 4-hydroxyphenyl), optionally substituted arylalkyl (for example, 1-phenylethyl), optionally substituted heterocyclylalkyl (for example, 1-pyridin-3-yl-ethyl or [1,4']bipiperidinyl), optionally substituted heterocyclyl (for example, 5-chloro-pyridin-3-yl or 1-methyl-piperidin-4-yl), optionally substituted alkoxy, alkylenedioxy (for example methylenedioxy), optionally substituted amino (for example, alkylamino, dialkylamino, optionally substituted dialkylamino (wherein each alkyl on the amino is optionally substituted)), optionally substituted amidino, optionally substituted aryloxy (for example, phenoxy), optionally substituted arylalkyloxy (for example, benzyloxy), carboxy (—$CO_2H$), carboalkoxy (that is, acyloxy or —$OC(=O)R$), carboxyalkyl (that is, esters or —$CO_2R$), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido.

The term "alkenyl" as used herein, means a straight or branched chain hydrocarbon containing from 2 to 10 carbons, unless otherwise specified, and containing at least one carbon-carbon double bond.

The term "alkoxy" as used herein, means an alkyl group, as defined herein, appended to the parent molecular moiety through an oxygen atom. The term "alkyl" as used herein, means a straight or branched chain hydrocarbon containing from 1 to 10 carbon atoms unless otherwise specified. The term alkyl includes both saturated and unsaturated hydrocarbons of from 1 to 10 carbon atoms. Saturated alkyl refers to hydrocarbon groups of, for example, 1-10 carbon atoms, and having no sites of unsaturation. Unsaturated alkyl refers to hydrocarbon groups of, for example, 1-10 carbon atoms, and having one or more sites of unsaturation, and includes both alkenyl and alkynyl groups. Alkyl groups may be optionally substituted as described herein.

The term "alkylene" refers to a bivalent alkyl group. The term "aryl," as used herein, means an aromatic hydrocarbon ring system containing at least one aromatic ring, e.g., a phenyl (i.e., monocyclic aryl), or a bicyclic ring system containing at least one aromatic hydrocarbon ring, e.g., phenyl, or an aromatic bicyclic ring containing only carbon atoms in the aromatic portion of the ring system. Preferred aryl groups have from 6-14 ring members, and more preferably from 6-10 ring members. Examples of aryl groups include, for example, phenyl, naphthyl, anthracenyl, azulenyl 1,2,3,4-tetrahydronaphthalenyl, indenyl, 2,3-dihydroindenyl, and biphenyl.

An "arylalkyl" group comprises an aryl group as defined herein covalently attached to an alkyl group, either of which independently is optionally substituted. Preferably, the arylalkyl group is aryl($C_1$-$C_6$)alkyl, including, without limitation, benzyl, phenethyl, and naphthylmethyl.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3).

The term "heteroaryl," as used herein, means a monocyclic heteroaryl or a bicyclic ring system containing at least one heteroaromatic ring. Preferred heteroaryl groups have from 5-14 ring members where from 1-4 of the ring members are hetero atoms selected from the group consisting of O, N, and S, the remaining ring atoms being C. More preferred heteroaryl groups have from 5-10 ring members where from 1-4 of the ring members are hetero atoms selected from the group consisting of O, N, and S, the remaining ring atoms being C.

The terms "heterocyclyl" and "heterocycloalkyl" as used herein, are interchangeable and mean a monocyclic heterocycle or a bicyclic heterocycle. Heterocycloalkyl aryl groups of the invention have from 3-14 ring members where from 1-4 of the ring members are hetero atoms selected from the group consisting of O, N, and S, the remaining ring atoms being C. More preferred heterocycloalkyl groups have from 5-10 ring members where from 1-4 of the ring members are hetero atoms selected from the group consisting of O, N, and S, the remaining ring atoms being C.

The aryl, cycloalkyl, heteroaryl, and heterocycloalkyl ring systems of the invention may be substituted with various groups as provided herein. Thus, any carbon atom present within a ring system and available for substitution may be further bonded to a variety of ring substituents, such as, for example, halogen, OH, $NO_2$, CN, $NH_2$, $C_1$-$C_8$ alkyl, $C_1$-$C_8$ alkoxy, NH($C_1$-$C_8$ alkyl), N($C_1$-$C_8$ alkyl)($C_1$-$C_8$ alkyl), $C_3$-$C_{10}$ cycloalkyl, ($C_3$-$C_{10}$ cycloalkyl)alkyl, ($C_3$-$C_{10}$ cycloalkyl)alkoxy, $C_2$-$C_9$ heterocycloalkyl, $C_1$-$C_8$ alkenyl, $C_1$-$C_8$ alkynyl, halo($C_1$-$C_8$)alkyl, halo($C_1$-$C_8$)alkoxy, oxo, amino($C_1$-$C_8$)alkyl, mono- and di($C_1$-$C_8$ alkyl)amino($C_1$-$C_8$)alkyl, $C_1$-$C_8$ acyl, $C_1$-$C_8$ acyloxy, $C_1$-$C_8$ sulfonyl, $C_1$-$C_8$ thio, $C_1$-$C_8$ sulfonamido, $C_1$-$C_8$ aminosulfonyl.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

Nitrogen protecting group refers to a protecting group or protective group that is introduced into a molecule by chemical modification of a functional group to prevent it from reacting in certain subsequent chemical reactions. A nitrogen protecting group is typically introduced during a protection or blocking step, and removed via deprotection.

In addition to presence of the $R_P$ group in the intermediates and polymers of the invention, protection of certain reactive functionalities may be necessary to achieve transformations necessary to prepare starting materials and intermediates useful in preparing the polymers of the invention. In general, the nature of and need for such protecting groups as well as the conditions necessary to attach and remove such groups will be apparent to those skilled in the art of organic synthesis. An authoritative account describing the many alternatives to the trained practitioner can be found in "Protective Groups in Organic Synthesis", T. W. Greene and P. G. M. Wuts, Third edition, Wiley, New York 1999. The protecting groups may be removed at a convenient subsequent stage using methods known from the art; Methods for removal of protecting groups are also described in the Greene and Wuts text.

Deprotection agent refers to a reagent, mixture of reagents, or set of conditions, including environmental conditions, that chemoselectively achieve or promote the removal of a protecting group from an atom or group of atoms. Deprotection conditions herein include a reagent, mixture of reagents, or set of conditions, including environmental conditions, that chemoselectively achieve or promote the removal of a the $R_P$ protecting group from the aniline nitrogen atoms in the polymer.

Depolymerization conditions refers to conditions or reactants that lead to depolymerization or degradation of the polymer. Depolymerization conditions include, but are not limited to, deprotection agents and conditions.

Linker, linker group, and linker unit refer to a unit that is covalently attached, directly or indirectly, to each of the hydroxyl groups of a bishydroxymethylaniline. Linkers are typically incorporated into the polymer molecule as described during the polymerization reaction between the bishydroxymethylaniline and a linking agent. The linker may be or include a group that when liberated from the polymer may participate in a chemical interaction with the surrounding environment, for example, biological activity.

"Pharmacological agent" and "therapeutic agent" as used herein, are interchangeable and refer to a compound, material, or composition of matter, which has a known or assumed biological activity and is suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

As noted above, in one aspect, the invention provides is a polymer of Formula I:

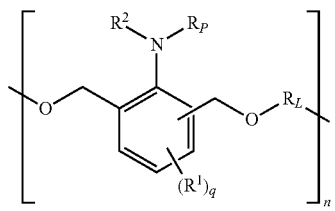

wherein
each $R_P$ is independently a nitrogen protecting group;
the —CH$_2$O—R$_L$— group is at the ortho or para position to N;
each $R^1$ is independently hydrogen, —CH$_2$O—R$_L$—, alkyl, aryl, alkoxy, arylalkyl, or halogen, provided that no more than one of $R^1$ is —CH$_2$O—R$_L$—, and when $R^1$ is —CH$_2$O—R$_L$— it is at the remaining para or ortho position relative to N;

q is 1, 2, or 3;
each $R_L$ is independently a linker;
each $R^2$ is independently hydrogen, alkyl, alkenyl, alkylalkoxy, aryl, or arylalkyl; and
n is from 2 to about 100,000.

Further disclosed is a polymer as described above, where each $R^1$ is independently hydrogen, alkyl, aryl, alkoxy, arylalkyl, or halogen; and
each $R_L$ is independently alkyl, alkenyl, —C(O)—, —C(O)-alkyl-(O)C—,
—C(O)-cycloalkyl-(O)C—, —C(O)-aryl-(O)C—, —C(O)-heteroaryl-(O)C—, —C(O)-cycloalkyl-alkyl-cycloalkyl-(O)C—, —C(O)-aryl-alkyl-aryl-(O)C—, —C(O)-alkyl-cycloalkyl-alkyl-(O)C—, —C(O)-alkyl-aryl-alkyl-(O)C—, —C(O)NR-alkyl-NR(O)C—, —C(O)NR-cycloalkyl-NR(O)C—, —C(O)NR-aryl-NR(O)C—, —C(O)NR-heteroaryl-NR(O)C—, —C(O)NR-cycloalkyl-alkyl-cycloalkyl-NR(O)C—, —C(O)NR-aryl-alkyl-aryl-NR(O)C—, —C(O)NR-alkyl-cycloalkyl-alkyl-NR(O)C—, —C(O)NR-alkyl-aryl-alkyl-NR(O)C—, —C(O)O-alkyl-O(O)C—, —C(O)O-cycloalkyl-O(O)C—, —C(O)O-aryl-O(O)C—, —C(O)O-heteroaryl-O(O)C—, —C(O)O-cycloalkyl-alkyl-cycloalkyl-O(O)C—, —C(O)O-aryl-alkyl-aryl-O(O)C—, —C(O)O-alkyl-cycloalkyl-alkyl-O(O)C—, —C(O)O-alkyl-aryl-alkyl-O(O)C—, —C(O)S-alkyl-S(O)C—, —C(O)S-cycloalkyl-S(O)C—, —C(O)S-aryl-S(O)C—, —C(O)S-heteroaryl-S(O)C—, —C(O)S-cycloalkyl-alkyl-cycloalkyl-S(O)C—, —C(O)S-aryl-alkyl-aryl-S(O)C—, —C(O)S-alkyl-cycloalkyl-alkyl-S(O)C—, —C(O)S-alkyl-aryl-alkyl-S(O)C—, —C(O)-alkyl-O-alkyl-(O)C—, —C(O)-cycloalkyl-O-cycloalkyl(O)C—, —C(O)-aryl-O-aryl-(O)C—, —C(O)-alkyl-NR-alkyl-(O)C—, —C(O)-cycloalkyl-NR-cycloalkyl(O)C—, —C(O)-aryl-NR-aryl-(O)C—, —C(O)-alkyl-S-alkyl-(O)C—, —C(O)-alkylene-S-alkylene-(O)C—, —C(O)-cycloalkyl-S-cycloalkyl(O)C—, —C(O)-aryl-S-aryl-(O)C—, —C(S)—, —C(S)-alkyl-(S)C—, —C(S)-alkylene-(S)C—, —C(S)-cycloalkyl-(S)C—, —C(S)-aryl-(S)C—, —C(S)-heteroaryl-(S)C—, —C(S)-cycloalkyl-alkyl-cycloalkyl-(S)C—, —C(S)-aryl-alkyl-aryl-(S)C—, —C(S)-alkyl-cycloalkyl-alkyl-(S)C—, —C(S)-alkyl-aryl-alkyl-(S)C—, —C(S)NR-alkyl-NR(S)C—, —C(S)NR-cycloalkyl-NR(S)C—, —C(S)NR-aryl-NR(S)C—, —C(S)NR-heteroaryl-NR(S)C—, —C(S)NR-cycloalkyl-alkyl-cycloalkyl-NR(S)C—, —C(S)NR-aryl-alkyl-aryl-NR(S)C—, —C(S)NR-alkyl-cycloalkyl-alkyl-NR(S)C—, —C(S)NR-alkyl-aryl-alkyl-NR(S)C—, —C(S)O-alkyl-O(S)C—, —C(S)O-cycloalkyl-O(S)C—, —C(S)O-aryl-O(S)C—, —C(S)O-heteroaryl-O(S)C—, —C(S)O-cycloalkyl-alkyl-cycloalkyl-O(S)C—, —C(S)O-aryl-alkyl-aryl-O(S)C—, —C(S)O-alkyl-cycloalkyl-alkyl-O(S)C—, —C(S)O-alkyl-aryl-alkyl-O(S)C—, —C(S)S-alkyl-S(S)C—, —C(S)S-cycloalkyl-S(S)C—, —C(S)S-aryl-S(S)C—, —C(S)S-heteroaryl-S(S)C—, —C(S)S-cycloalkyl-alkyl-cycloalkyl-S(S)C—, —C(S)S-aryl-alkyl-aryl-S(S)C—, —C(S)S-alkyl-cycloalkyl-alkyl-S(S)C—, —C(S)S-alkyl-aryl-alkyl-S(S)C—, —C(S)-alkyl-O-alkyl-(S)C—, —C(S)-cycloalkyl-O-cycloalkyl(S)C—, —C(S—C(S)-aryl-O-aryl-(S)C—, —C(S)-alkyl-NR-alkyl-(S)C—, —C(S)-cycloalkyl-NR-cycloalkyl(S)C—, —C(S)-aryl-NR-aryl-(S)C—, —C(S)-alkyl-S-alkyl-(S)C—, —C(S)-cycloalkyl-S-cycloalkyl(S)C—, —C(S)-aryl-S-aryl-(S)C—, —C(S)-alkyl-(O)C—, —C(S)-cycloalkyl-(O)C—, —C(S)- aryl-(O)C—, —C(S)-heteroaryl-(O)C—, —C(S)-cycloalkyl-alkyl-cycloalkyl-(O)C—, —C(S)-aryl-alkyl-aryl-(O)C—, —C(S)-alkyl-cycloalkyl-alkyl-(O)C—, —C(S)-alkyl-aryl-alkyl-(O)C—, —C(S)NR-alkyl-NR(O)C—, —C(S)NR-cycloalkyl-NR(O)C—, —C(S)NR-aryl-NR(O)C—, —C(S)NR-heteroaryl-NR(O)C—, —C(S)NR-cycloalkyl-alkyl-cycloalkyl-NR(O)C—, —C(S)NR-aryl-alkyl-aryl-NR(O)C—, —C(S)NR-alkyl-cycloalkyl-alkyl-NR(O)C—, —C(S)NR-alkyl-aryl-alkyl-NR(O)C—, —C(S)O-alkyl-O(O)C—, —C(S)O-cycloalkyl-O(O)C—, —C(S)O-aryl-O(O)C—, —C(S)O-heteroaryl-O(O)C—, —C(S)O-cycloalkyl-alkyl-cycloalkyl-O(O)C—, —C(S) O-aryl-alkyl-aryl-O(O)C—, —C(S)O-alkyl-cycloalkyl-alkyl-O(O)C—, —C(S)O-alkyl-aryl-alkyl-O(O)C—, —C(S)S-alkyl-S(O)C—, —C(S)S-cycloalkyl-S(O)C—, —C(S)S-aryl-S(O)C—, —C(S)S-hetero aryl-S(O)C—, —C(S)S-cycloalkyl-alkyl-cycloalkyl-S(O)C—, —C(S)S-aryl-alkyl-aryl-S(O)C—, —C(S)S-alkyl-cycloalkyl-alkyl-S(O)C—, —C(S)S-alkyl-aryl-alkyl-S(O)C—, —C(S)-alkyl-O-alkyl-(O)C—, —C(S)-cycloalkyl-O-cycloalkyl(O)C—, —C(S)-aryl-O-aryl-(O)C—, —C(S)-alkyl-NR-alkyl-(O)C—, —C(S)-cycloalkyl-NR-cycloalkyl(O)C—, —C(S)-aryl-NR-aryl-(O)C—, —C(S)-alkyl-S-alkyl-(O)C—, —C(S)-cycloalkyl-S-cycloalkyl(O)C—, —C(S)-aryl-S-aryl-(O)C—, or any combination of the above, where R is H, alkyl, cycloalkyl, aryl or arylalkyl.

Further disclosed is a polymer as described above, where each $R_L$ is independently alkyl, alkenyl, —C(O)—, —C(O)-alkyl-(O)C—, —C(O)-cycloalkyl-(O)C—, —C(O)-aryl-(O)C—, —C(O)-heteroaryl-(O)C—, —C(O)-cycloalkyl-alkyl-cycloalkyl-(O)C—, —C(O)-aryl-alkyl-aryl-(O)C—, —C(O)-alkyl-cycloalkyl-alkyl-(O)C—, —C(O)-alkyl-aryl-alkyl-(O)C—, —C(O)NR-alkyl-NR(O)C—, —C(O)NR-cycloalkyl-NR(O)C—, —C(O)NR-aryl-NR(O)C—, —C(O)NR-heteroaryl-NR(O)C—, —C(O)NR-cycloalkyl-alkyl-cycloalkyl-NR(O)C—, —C(O)NR-aryl-alkyl-aryl-NR(O)C—, —C(O)NR-alkyl-cycloalkyl-alkyl-NR(O)C—, —C(O)NR-alkyl-aryl-alkyl-NR(O)C—, —C(O)O-alkyl-O(O)C—, —C(O)O-cycloalkyl-O(O)C—, —C(O)O-aryl-O(O)C—, —C(O)O-heteroaryl-O(O)C—, —C(O)O-cycloalkyl-alkyl-cycloalkyl-O(O)C—, —C(O)O-aryl-alkyl-aryl-O(O)C—, —C(O)O-alkyl-cycloalkyl-alkyl-O(O)C—, —C(O)O-alkyl-aryl-alkyl-O(O)C—, —C(O)S-alkyl-S(O)C—, —C(O)S-cycloalkyl-S(O)C—, —C(O)S-aryl-S(O)C—, —C(O)S-heteroaryl-S(O)C—, —C(O)S-cycloalkyl-alkyl-cycloalkyl-S(O)C—, —C(O)S-aryl-alkyl-aryl-S(O)C—, —C(O)S-alkyl-cycloalkyl-alkyl-S(O)C—, —C(O)S-alkyl-aryl-alkyl-S(O)C—, —C(O)-alkyl-O-alkyl-(O)C—, —C(O)-cycloalkyl-O-cycloalkyl(O)C—, —C(O)-aryl-O-aryl-(O)C—, —C(O)-alkyl-NR-alkyl-(O)C—, —C(O)-cycloalkyl-NR-cycloalkyl(O)C—, —C(O)-aryl-NR-aryl-(O)C—, —C(O)-alkyl-S-alkyl-(O)C—, —C(O)-cycloalkyl-S-cycloalkyl(O)C—, —C(O)-aryl-S-aryl-(O)C—, where R is H, alkyl, cycloalkyl, aryl or arylalkyl.

Further disclosed is a polymer as described above, where each $R_L$ is independently:

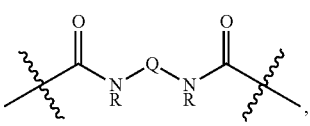

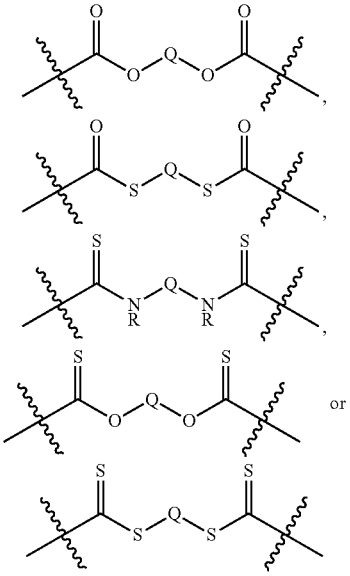

where

Q is aryl, alkyl, cycloalkyl, alkyl-aryl-alkyl, aryl-alkyl-aryl, or cycloalkyl-alkyl-cycloalkyl, each of which is optionally substituted with one or more of aryl, alkyl, alkoxy, amino, aminoalkyl, cycloalkyl, oxo, or halogen; and R is H, alkyl, cycloalkyl, aryl or arylalkyl.

Further disclosed is a polymer as described above, where each $R_L$ is independently:

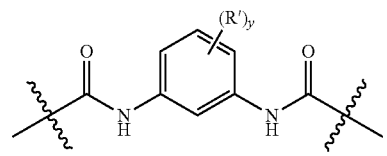

where

R' at any position is H, alkyl, aryl, alkoxy, arylalkyl, haloalkyl, or halogen; and y is 1, 2, 3 or 4.

Further disclosed is a polymer as described above, where R' is methyl ethyl, phenyl, fluoro, chloro, bromo, iodo, methoxy, ethoxy, chloromethyl, or benzyl.

Further disclosed is a polymer as described above, where each $R_L$ is independently:

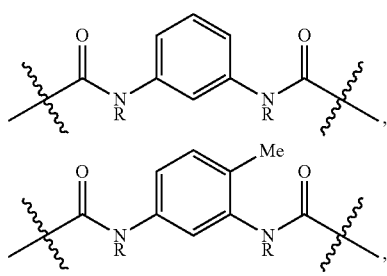

-continued

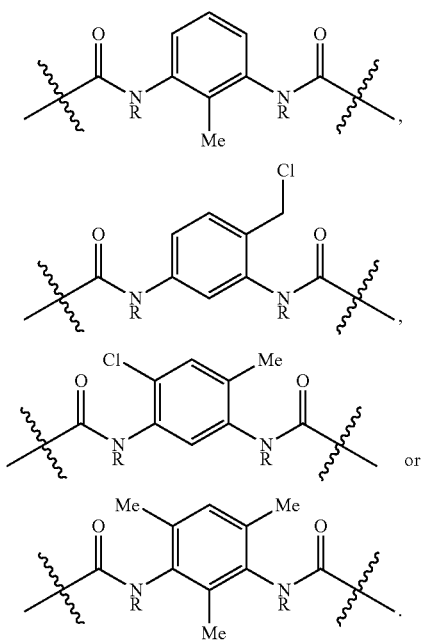

Further disclosed is a polymer as described above, where each $R_L$ is independently:

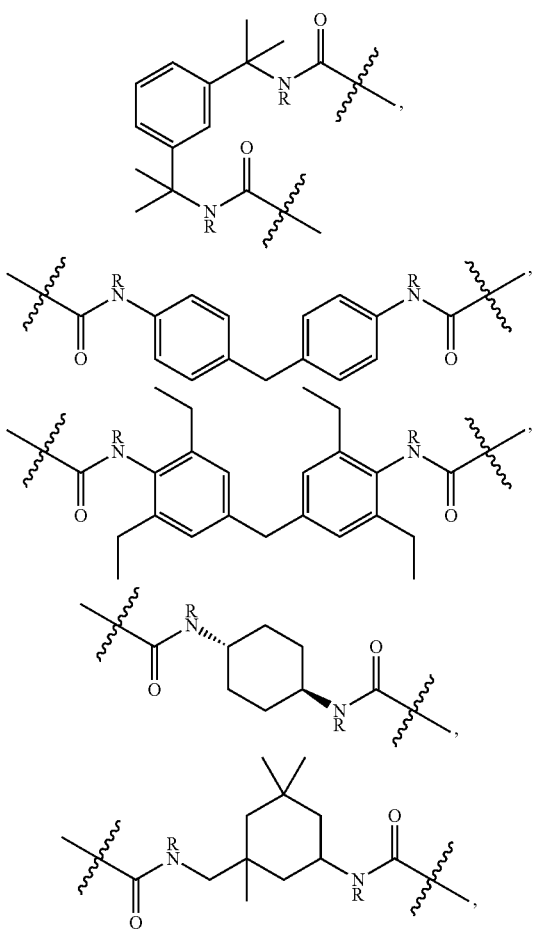

-continued

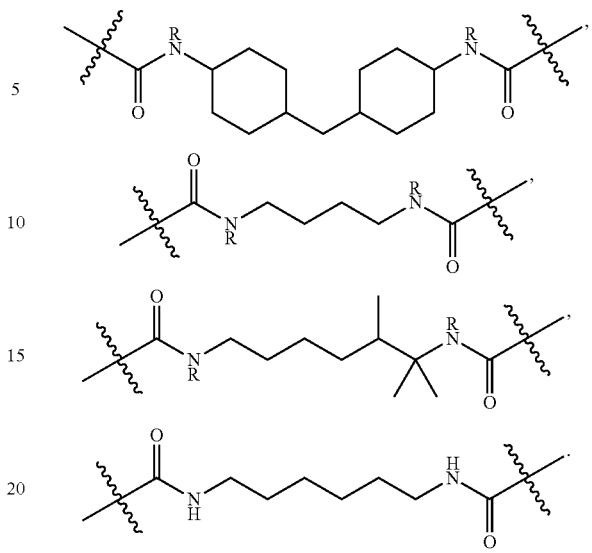

Further disclosed is a polymer as described above, where each $R_L$ is independently:

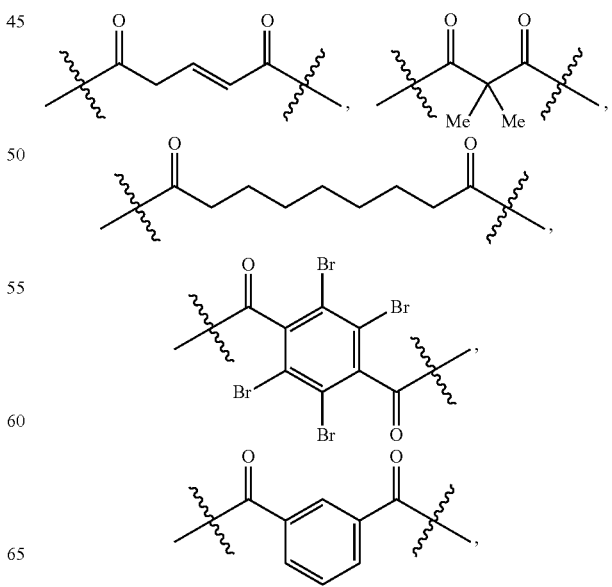

where D is aryl, alkyl, cycloalkyl, alkenyl, cycloalkenyl, heterocyclyl, heteroalkyl, or heteroaryl, each of which is optionally substituted with one or more of aryl, alkyl, alkoxy, nitro, amino, aminoalkyl, cycloalkyl, oxo, imino, or halogen.

Further disclosed is a polymer as described above, where each $R_L$ is independently:

-continued

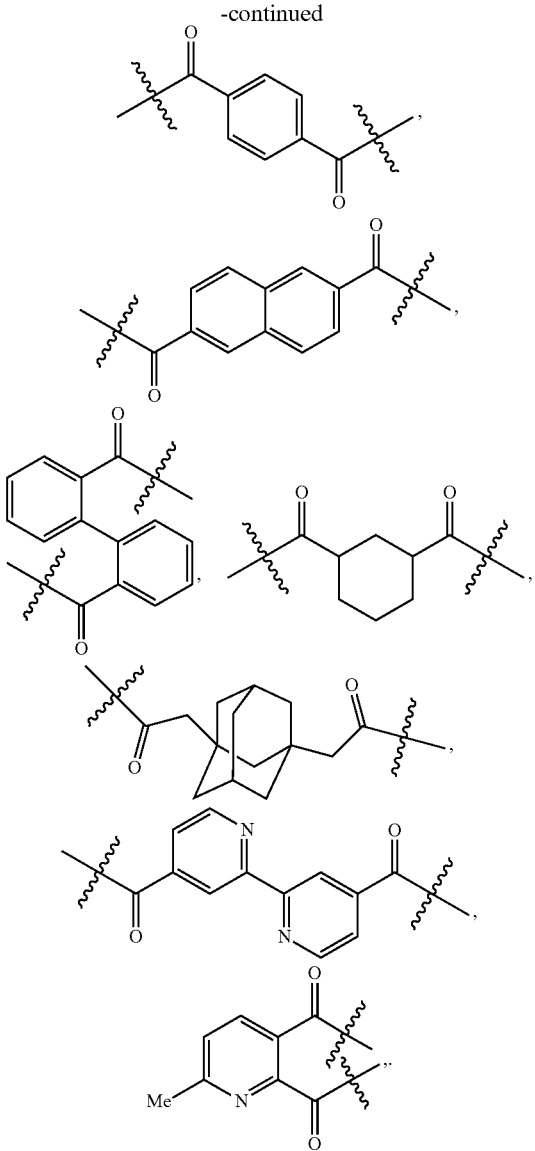

Further disclosed is a polymer as described above, where each $R_L$ is independently:

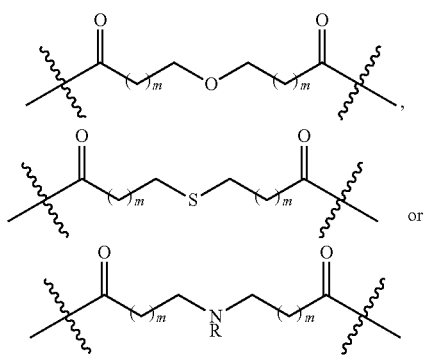

where
each m independently is from 1 to about 100; and
R is H, alkyl, cycloalkyl, aryl or arylalkyl.

Further disclosed is a polymer as described above, where each $R_L$ is independently:

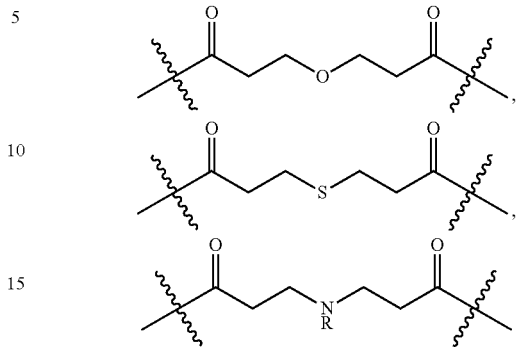

where R is H, alkyl, cycloalkyl, aryl or arylalkyl.

Further disclosed is a polymer as described above, where R is H, methyl, ethyl, phenyl, cyclohexyl, cyclopentyl, or benzyl.

In certain embodiments, the $R_L$ groups are all derived from the same linking agent and all the $R_L$ groups in the polymer are therefore the same. In other embodiments, the polymer will be formed using two or more different linking agents resulting in a polymer that has different $R_L$ groups throughout its backbone.

Further disclosed is a polymer as described above where $R_L$ comprises a unit that upon release from the polymer backbone has utility as a therapeutic agent, a chemotherapy agent, a detectable agent, a fluorescent agent, a radioactive agent, and magnetic agent, a chromophore, a phosphorescent agent, a contrast agent, a heavy metal cluster, a chemical agent, an agrochemical agent, a chemosensitizing agent, a herbicide, a pesticide, or a fungicide.

In still other embodiments, $R_L$ comprises a unit that upon release from the polymer backbone has utility as an acaricide, algaecide, antifeedant, avicide, bactericide, bird repellent, chemosterilant, defoliant, desiccant, disinfectant, fungicide, herbicide safener, herbicide, insect attractant, insecticide, insect repellent, mammal repellent, mating disrupter, molluscicide, nematicide, plant activator, plant growth regulator, rodenticide, semiochemical, synergist, or virucide.

In certain embodiments, the $R_L$ group is derived from a molecule that comprises a unit with two or more hydroxyl moieties or derivatives thereof.

In certain embodiments, the $R_L$ group is derived from a molecule that comprises a unit with two or more amino moieties or derivatives thereof.

In certain embodiments, the $R_L$ group is derived from a molecule that comprises a unit with two or more thiol moieties or derivatives thereof.

In certain embodiments, the $R_L$ group is derived from a molecule that comprises a unit with two or more carboxylic acid moieties or derivatives thereof.

In certain embodiments, the $R_L$ group is derived from a molecule that comprises two functional groups, each of which is capable of forming a covalent bond to result in a compound of Formula I, optionally through a linker. In some embodiments, the functional groups are independently selected from hydroxyl, amino, thio and carboxylic acid groups, and derivatives thereof.

In certain embodiments, the $R_L$ group comprises a biologically active unit having two or more functional groups, each of which is capable of forming a covalent bond to result in a compound of Formula I, optionally through a linker. In some embodiments, the functional groups are independently selected from hydroxyl, amino, thio and carboxylic acid groups, and derivatives thereof.

In other embodiments, the $R_L$ comprises a non-biologically active unit containing two or more hydroxyl moieties; a non-biologically active unit containing two or more amino moieties, a non-biologically active unit containing two or more thiol moieties, or a non-biologically active unit containing two or more carboxylic acid moieties.

In other embodiments, the $R_L$ group comprises a biologically active unit containing two or more hydroxyl groups; a biologically active unit containing two or more amino groups, a biologically active unit containing two or more thiol groups, or a biologically active unit containing two or more carboxylic acid groups.

In certain embodiments, the $R_L$ group is derived from a molecule that comprises chromophore that can be used for the quantification of the deprotection agent.

Further disclosed is a polymer as described above, where each $R_P$ is independently —X—Y—Z,
where
X is —CO—, —CO$_2$—, —SO$_2$—, or —C(O)NR"—, where R" is H, alkyl, cycloalkyl, aryl or arylalkyl;
Y is —CH$_2$—, —CH$_2$CH$_2$—, or a bond; and
Z is aryl, alkyl, cycloalkyl, alkenyl, cycloalkenyl, heterocyclic, C(O)alkyl, alkyl-disulfide, or NR$^{23}$R$^{24}$, each of which is optionally substituted with one or more of aryl, alkyl, alkoxy, nitro, amino, aminoalkyl, cycloalkyl, oxo, imino, or halogen.

Further disclosed is a polymer as described above, where each $R_P$ is independently:

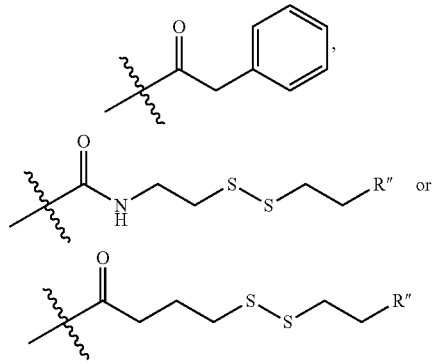

where R" is independently hydrogen, alkyl, aryl, alkoxy, arylalkyl, halogen, or azido.

In certain embodiments, $R^2$ is not present and $R_P$ is:

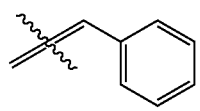 [SMILES: *=Cc1ccccc1]

Further disclosed is a polymer as described above, where each $R_P$ is independently a group of Formula (a):

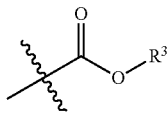

(a)

where $R^3$ is alkyl, cycloalkyl, aryl, heterocyclyl, heteroaryl, or alkenyl, each of which is optionally substituted at one or more positions.

Further disclosed is a polymer as described above, where $R^3$ is tert-butyl.

Further disclosed is a polymer as described above, where $R^3$ is:

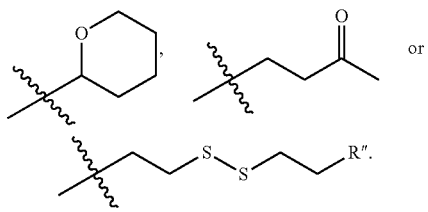

Further disclosed is a polymer as described above, where each $R_P$ is independently a group of Formula (b):

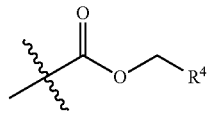

(b)

where $R^4$ is an optionally substituted aryl, heterocyclic, or cycloalkenyl ring.

Further disclosed is a polymer as described above, where the cycloalkenyl ring is a coumarin, which is optionally substituted with one or more of alkyl, alkoxy, hydroxyl, nitro, amino, aminoalkyl, oxo, imino, or halogen.

Further disclosed is a polymer as described above, where the optionally substituted coumarin is of the Formula:

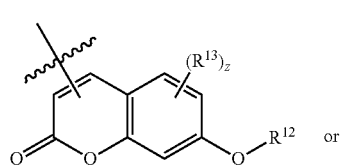

b1

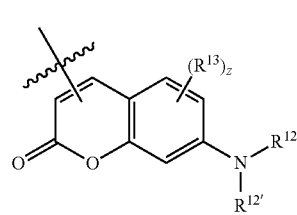

b2 where
$R^{12}$ and $R^{12'}$ are alkyl, aryl, arylalkyl, or alkoxyalkyl; and
$R^{13}$ is nitro, fluoro, chloro, bromo, iodo; and
z is 1, 2, 3 or 4.

Further disclosed is a polymer as described above, where the substituted coumarin is:

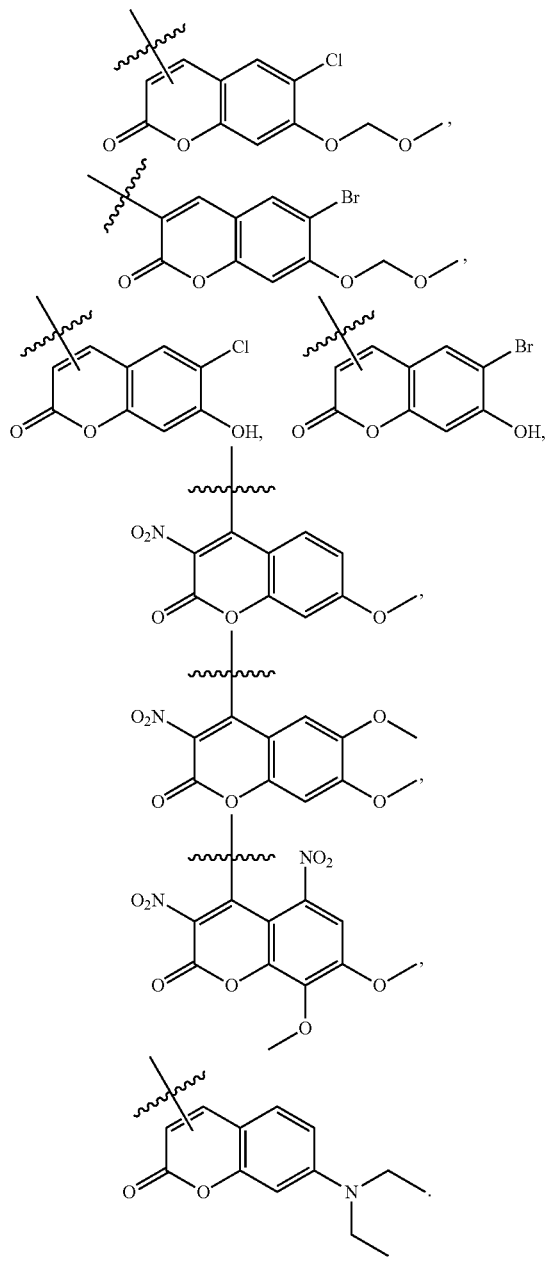

Further disclosed is a polymer as described above, where R⁴ is of the Formula:

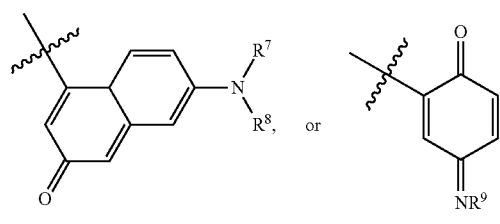

where

R⁷, R⁸ and R⁹ are individually H, alkyl, benzyl, substituted benzyl, arylsulfonyl or carbamoyl.

Further disclosed is a polymer as described above, where R⁴ is aryl, optionally substituted at two adjacent positions forming a ring, or with one or more of alkoxy, aryl, nitro, or —B(OR¹⁰)(OR¹¹), where R¹⁰ and R¹¹ are alkyl, cycloalkyl, aryl, or R¹⁰ and R¹¹ together with the atoms to which they are connected combine to form a ring.

Further disclosed is a polymer as described above, where R⁴ is of the Formula:

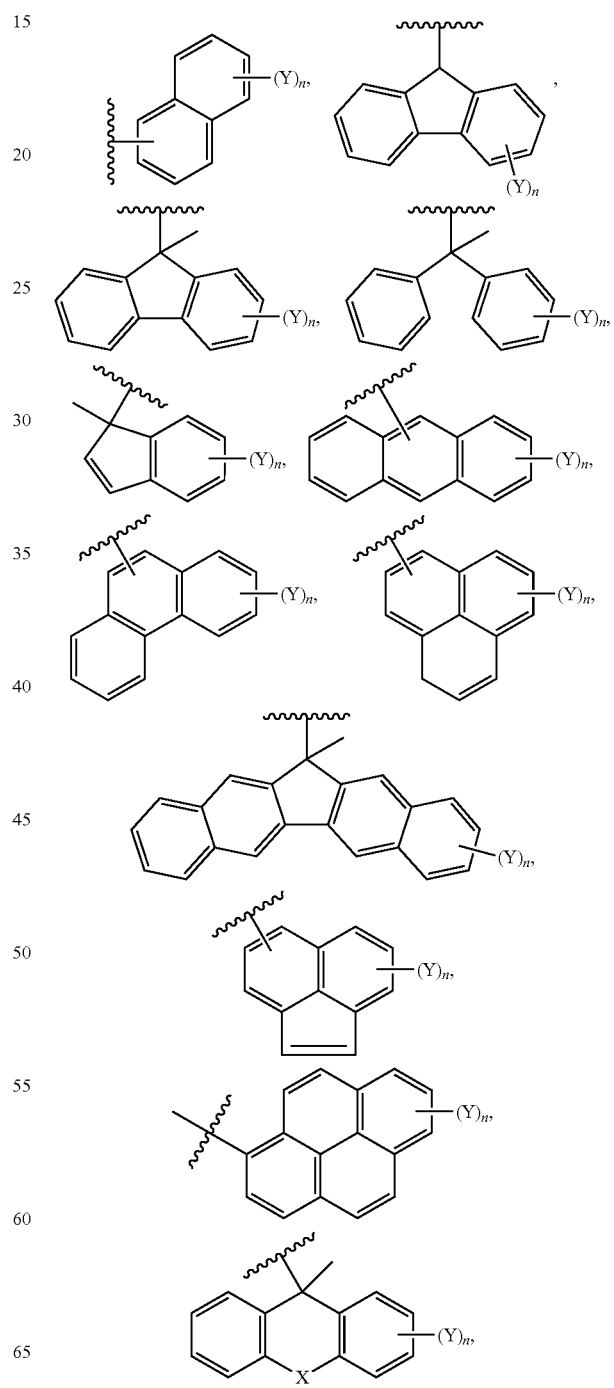

-continued

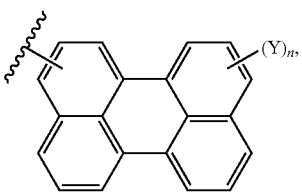

or where

Y is H, alkyl, alkoxy, aryloxy, haloalkyl or halogen; and n is 1-12; and

X is oxygen, sulfur, $CH_2$, $CH_2CH_2$, $CH=CH$ or NR where R is hydrogen, alkyl, or arylalkyl.

Further disclosed is a polymer as described above, where $R^4$ is: 9H-fluoren-9-yl or pyren-1-yl.

Further disclosed is a polymer as described above, where $R^4$ is:

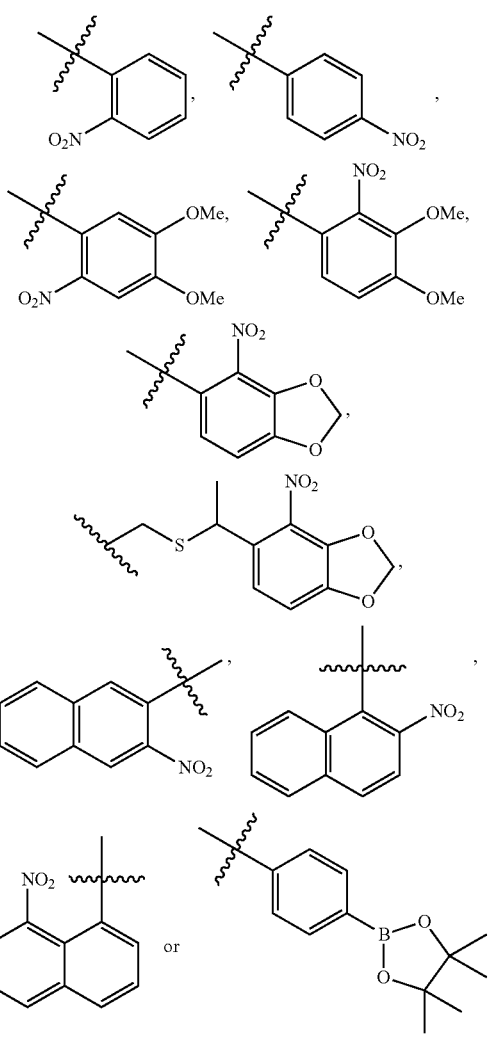

Further disclosed is a polymer as described above, where each $R_P$ is independently a group of Formula (c):

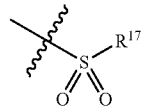
(c)

where $R^{17}$ is an optionally substituted aryl or heteroaryl ring.

Further disclosed is a polymer as described above, where $R^{17}$ is an optionally substituted phenyl or pyridyl ring.

Further disclosed is a polymer as described above, where $R^{17}$ is of the Formula:

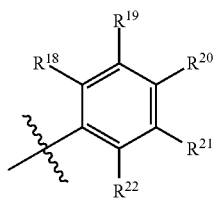

where $R^{18}$-$R^{22}$ are independently H, alkyl, alkoxy, nitro or halogen.

Further disclosed is a polymer as described above, where $R^{20}$ is methyl or nitro.

Further disclosed is a polymer as described above, where $R^{20}$ and $R^{18}$ are nitro.

Further disclosed is a polymer as described above, where each $R_P$ is independently a group of Formula (d):

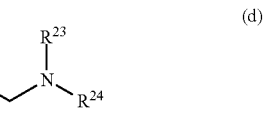
(d)

where $R^{23}$ is hydrogen or optionally substituted alkyl or aryl; and
$R^{24}$ is any group of Formula:

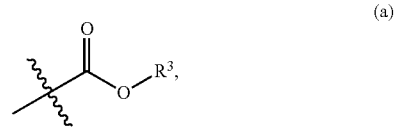
(a)

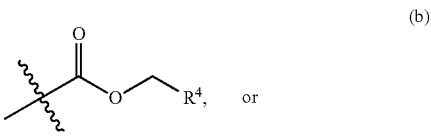
(b)

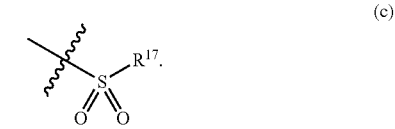
(c)

In certain embodiments, the $R_P$ groups are all derived from the same protecting agent or electrophile ($R_P$—X), (as described below) and all the resulting $R_P$ groups in the polymer are therefore the same. In other embodiments, the polymer will be formed using two or more different electrophiles resulting in a polymer that has different $R_P$ groups.

Further disclosed is a polymer as described above, where $R^1$ is methyl and is in the para position relative to N.

Further disclosed is a polymer as described above, where $R^2$ is methyl, ethyl, phenyl or benzyl.

Further disclosed is a polymer as described above, with a number average molecular weight between about 1 and about 1,000 kDa.

Further disclosed is a polymer as described above, with a number average molecular weight of:

| Lower Limit Molecular Weight (kDa) | Upper Limit Molecular\ Weight (kDa) |
|---|---|
| 1 | 10 |
| 10 | 20 |
| 20 | 30 |
| 30 | 40 |
| 40 | 50 |
| 50 | 60 |
| 60 | 70 |
| 70 | 80 |
| 80 | 90 |
| 90 | 100 |
| 100 | 110 |
| 110 | 120 |
| 120 | 130 |
| 130 | 140 |
| 140 | 150 |
| 150 | 160 |
| 160 | 170 |
| 170 | 180 |
| 180 | 190 |
| 190 | 200 |
| 200 | 210 |
| 210 | 220 |
| 220 | 230 |
| 230 | 240 |
| 240 | 250 |
| 250 | 300 |
| 300 | 350 |
| 350 | 400 |
| 400 | 450 |
| 450 | 500 |
| 500 | 550 |
| 550 | 600 |
| 600 | 650 |
| 650 | 700 |
| 700 | 750 |
| 750 | 800 |
| 800 | 850 |
| 850 | 900 |
| 900 | 950 |
| 950 | 1000 |

Further disclosed is a polymer as described above, in the form of an oligomer, dendrimer, cross-linked network, strand, film, fiber, mixture, resin, adhesive, coating, hydrogel, organogel or particle.

Also disclosed is a method for making a polymer of Formula I, comprising:

(a) mixing a compound of Formula II:

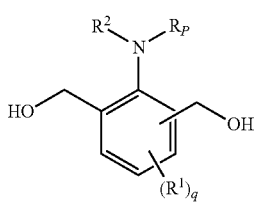

II where $R^2$ is hydrogen, alkyl, alkenyl, alkyl-alkoxy, aryl, or arylalkyl;

q is 1, 2, or 3;

each $R^1$ is independently hydrogen, —CH$_2$OH, alkyl, aryl, alkoxy, arylalkyl, or halogen; provided that no more than one of $R^1$ is —CH$_2$OH, and when $R^1$ is —CH$_2$OH it is at the para position and/or remaining ortho position relative to N; with one or more linking agents; and (b) isolating a polymer of Formula I.

Also disclosed is a method for making a compound of Formula III:

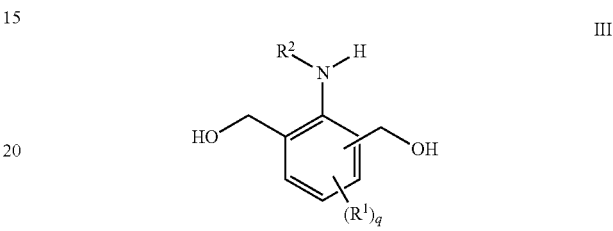

III where $R^2$ is hydrogen, alkyl, alkenyl, alkyl-alkoxy, aryl, or arylalkyl;

q is 1, 2, or 3; and each $R^1$ is independently hydrogen, —CH$_2$OH, alkyl, aryl, alkoxy, arylalkyl, or halogen; provided that no more than one of $R^1$ is —CH$_2$OH, and when $R^1$ is —CH$_2$OH it is at the para position and/or remaining ortho position relative to N; comprising:

(a) deprotecting a polymer of Formula I; and (b) isolating a compound of Formula III.

Further disclosed is a method for making a compound of Formula III, where the deprotecting is carried out by one or more of: electromagnetic radiation, ultrasonic radiation, electrochemical reaction, oxidation, reduction, acidic conditions, basic conditions, enzymatic cleavage, a biologic catalyst or nucleophilic displacement.

Further disclosed is a method as described above, where the electromagnetic radiation is in the ultraviolet range. Further disclosed is a method as described above, where the electromagnetic radiation is in the near-infrared range. Further disclosed is a method as described above, where the electromagnetic radiation is in the ultrasound range. Further disclosed is a method as described above, where the electromagnetic radiation is in the visible light range. Further disclosed is a method as described above, where the polymer is subjected to electromagnetic radiation at 0.001-100 W/cm$^2$ for 0.1-1000 minutes, preferably 0.01 to 10 W/cm$^2$, more preferably 0.03 to 0.1 W/cm$^2$ for 1 to 500 minutes, more preferably 30 to 240 minutes.

Further disclosed is a method as described above, where the acidic conditions include but are not limited to a mixture comprising trifluoroacetic acid, hydrochloric acid, sulfuric acid, nitric acid, phosphoric acid, boric acid, methanesulfonic acid, p-toluenesulfonic acid, trifluoromethanesulfonic acid, acetic acid, citric acid, formic acid, oxalic acid, gluconic acid, lactic acid, tartaric acid, ascorbic acid, or camphor sulfonic acid.

Further disclosed is a method as described above, where the basic conditions include but are not limited to a mixture comprising sodium hydroxide, potassium hydroxide, cesium hydroxide, lithium hydroxide, sodium carbonate, sodium bicarbonate, pyridine, pyrimidine, pyrazine, pyridazine, piperidine, pyrrolidine, piperazine, morpholine, imidazole, benzimidazole, histidine, or methylamine.

Further disclosed is a method as described above, where the oxidation conditions include but are not limited to a mixture comprising hydrogen peroxide, tert-butyl hydrogen peroxide, carbamide peroxide, m-chloroperoxybenzoic acid, peroxyacetic acid, peroxytrifluoroacetic acid.

Further disclosed is a method as described above, where the reduction conditions include but are not limited to a mixture comprising thiol containing compounds, sodium borohydride, metal powder, low valence metal ions, Nascent (atomic) hydrogen, sodium amalgam, Tin(II) chloride, hydrazine, zinc-mercury amalgam (Zn(Hg)), diisobutylaluminum hydride (DIBAH), Lindlar catalyst, oxalic acid, formic acid, ascorbic acid, phosphites, hypophosphites, phosphorous acid, dithiothreitol (DTT), and compounds containing the $Fe^{2+}$ ion, such as iron(II) sulfate.

Further disclosed is a method as described above, where the enzymatic cleavage or biologic catalyst comprises an enzyme or protein, such as, for example, bovine serum albumin or Penicillin G Amidase, or a biological molecule, such as, for example, DNA or RNA.

Also disclosed is a method for making a compound of Formula IV: H—X—$R_L$—X—H (IV) where
X is independently —O—, —$NR^2$, or S; and
$R_L$ and $R^2$ are as described above; comprising:
(a) deprotecting a polymer of Formula I; and
(b) isolating a compound of Formula IV.

Further disclosed is a method for making a compound of Formula IV from the deprotection of a polymer of Formula I, where the resulting compound of Formula IV undergoes one or more decarboxylations to form a compound of formula $R_L'$. For example, a polymer of Formula I of the structure:

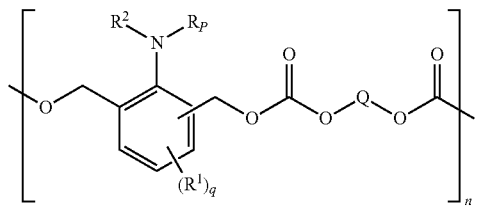

has a $R_L$ group of the structure:

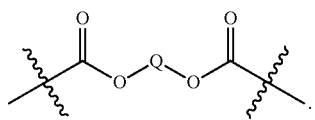

When the polymer is deprotected, the resulting compound of Formula IV is of the structure: $HO_2C$—O-Q-O—$CO_2H$, which may undergo decarboxylation to provide a compound of Formula $R_L'$ of the structure: HO-Q-OH.

As noted above, the polymer and the material or substance may be in combination as a mixture, and the mixture may be in any of various forms, e.g., layer, fiber, particle, coating, or capsule. The mixtures of the polymer and a substance can be made via a variety of technologies. For example, particles or capsules may be made by (a) contacting a polymer of the invention with a substance and (b) forming particles. A representative procedure for manufacturing polymer capsules containing a substance is hot melt encapsulation. Another representative procedure for making polymer capsules or particles containing a substance is dissolution encapsulation, i.e., a method comprising dissolving a polymer of the invention and the substance in a solvent; and removing the solvent to generate nanoparticles of the polymer containing the agent.

Encapsulation methodologies suitable for use with the invention may be adapted to produce particles and capsules of various sizes, including microcapsules and nanocapsules.

Representative synthetic procedures for the preparation of compounds of the invention are outlined below. Substituents carry the same meaning as defined above, unless otherwise noted.

Scheme 1

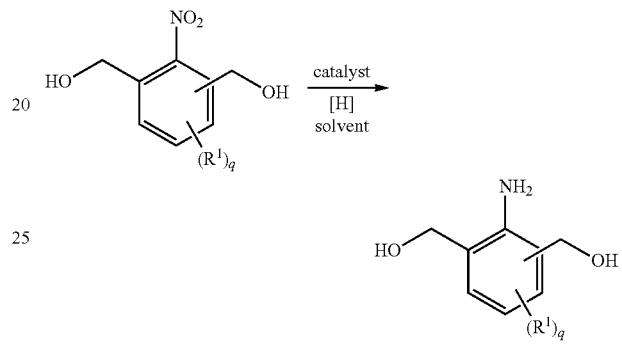

Scheme 1 illustrates a representative method for the formation of a hydroxymethyl anilines. An optionally substituted bishydroxynitrobenzene may be subjected to reduction conditions to provide the corresponding hydroxymethyl aniline. Reductions conditions typically comprise a catalyst, for example, palladium, platinum, nickel, ruthenium, rhodium or iridium, a hydrogen source, for example, hydrogen gas, hydrazine, dihydronaphthalene, dihydroanthracene, isopropanol, formic acid, cyclohexene or cyclohexadiene. Reactions are typically performed in a solvent, such as an alcohol, for example, methanol, ethanol, or isopropanol, or a chlorinated solvent, for example, dichloromethane, chloroform, or a non-chlorinated solvent, for example, tetrahydrofuran or ethyl acetate, or under neat reaction conditions.

Scheme 2

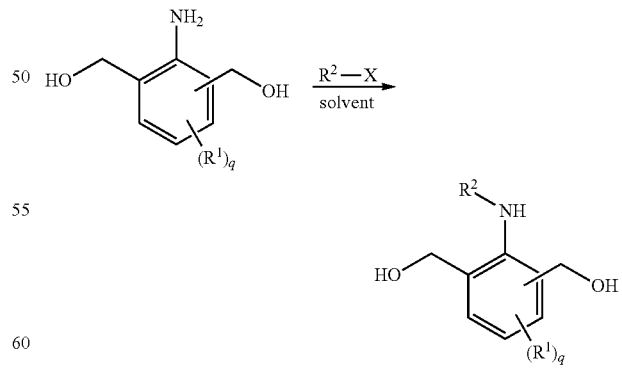

The $R^2$ nitrogen substituent is optionally introduced through reaction of the free amine of the hydroxymethyl aniline and an electrophile, $R^2$—X, which comprises the functionality to be covalently bonded to the aniline nitrogen ($R^2$), and a leaving group (X). $R^2$ comprises an alkyl, such as methyl or ethyl, alkenyl, such as allyl, alkyl-alkoxy, such as methoxyethyl ether, aryl, such as para-methoxy phenyl or arylalkyl, such as benzyl. The leaving group can vary from halogen, such as iodo, bromo, chloro, to anhydride, p-toluenesulfonate, methanesulfonate, trifluoromethanesulfonate or amine salts, such as 4-dimethylaminopyridine or imidazolium. For the synthesis of hydroxymethylanilines where $R^2$=H, this operation is not performed.

Scheme 4 illustrates the synthesis of degradable polymers. The protected hydroxymethylaniline is treated with a linking agent under polymerization conditions to afford a polymer with repeating units of the spacer covalently bound to the linker. The reaction is carried out in the presence of a polymerization additive, such as dibutyltin dilaurate (DBTL) or an amine, such as 4-dimethylamino pyridine, pyridine, or imidazole, at ambient or elevated temperature, in a suitable polar, aprotic solvent, such as dichloromethane, chloroform, or N,N-dimethylformamide. X comprises a leaving group that can be displaced by the alcohol of the hydroxymethylaniline under the reaction conditions. Isocyanate linking agents can be used directly in the reaction. XC(O/S)-linking agents may be purchased or synthesized from the corresponding carboxylic acid using procedures known to those of skill in the art.

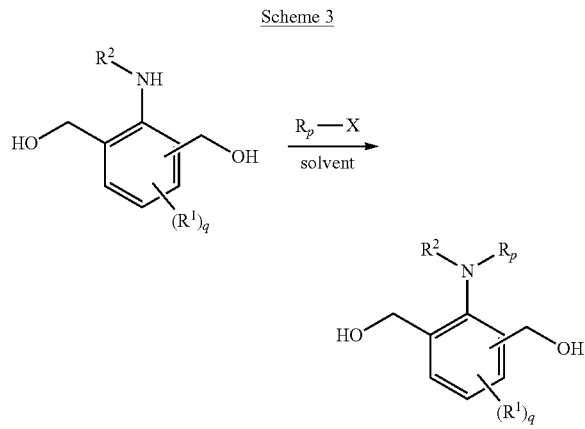

Scheme 3

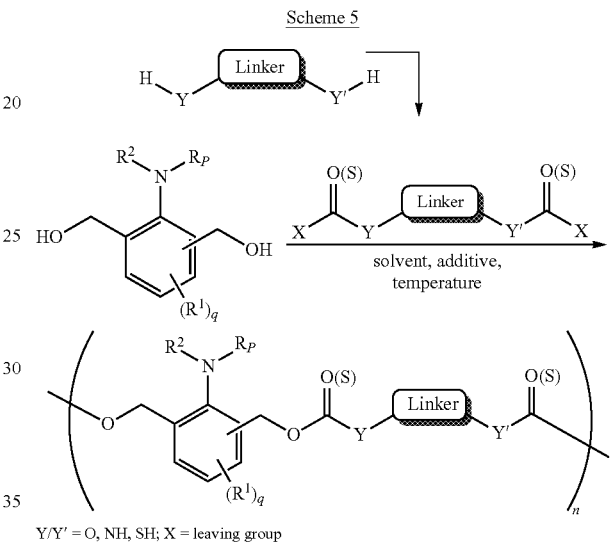

Scheme 5

Scheme 3 shows the synthesis of protected hydroxymethylaniline spacer units. The hydroxymethylaniline is treated with an electrophile ($R_P$—X) comprising the desired protecting group ($R_P$) and a leaving group (X). The electrophile is selected from a wide variety of groups, normally chosen for their ability to remain unreactive to most conditions, and reactive only to a specific set of deprotection conditions. The leaving group can vary from halogen, such as iodo, bromo, chloro, to anhydride, p-toluenesulfonate, methanesulfonate, trifluoromethanesulfonate or amine salts, such as 4-dimethylaminopyridine or imidazolium.

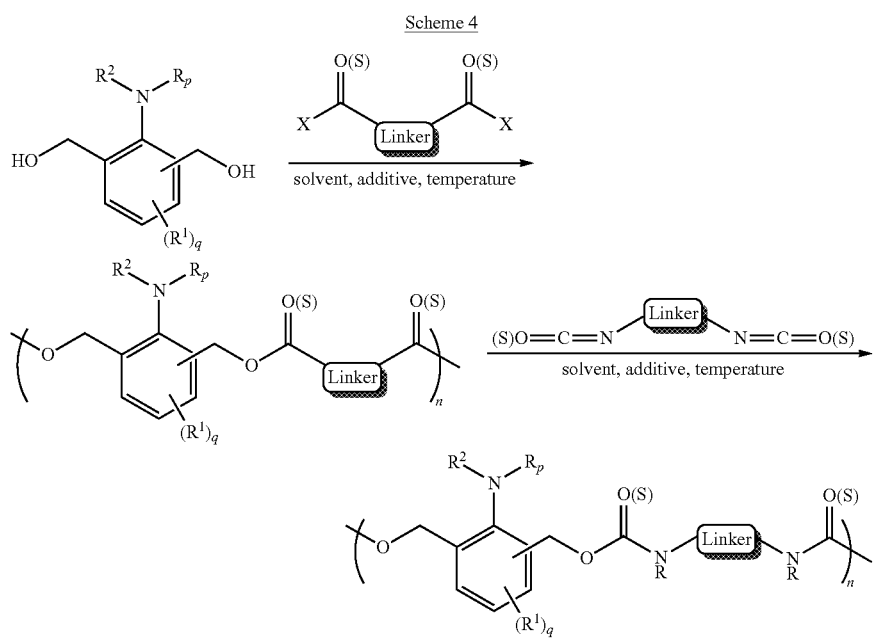

Scheme 4

Scheme 5 shows the synthesis of polymers with linking agents containing dithiol, diol or diamino functional groups that may have to be activated prior to reaction with the hydroxymethylaniline spacer. Activation is accomplished by conversion of the linking agent functional groups (Y/Y') to, for example, the corresponding acid chloride. These conversions are well known in the chemical literature and can be accomplished with, for example, phosgene. Y and Y' independently comprise O, S, or NH. X is a leaving group suitable to be displaced by the alcohol of the hydroxymethylaniline under the reaction conditions.

Representative isocyanates that can be used as linking agents directly in the polymerization reaction include but are not limited to the following: 1,3-bis(isocyanatomethyl)cyclohexane, 1,4-diisocyanatobutane, hexamethylene diisocyanate, tolylene-2,6-diisocyanate, 1,3-bis(1-isocyanato-1-methylethyl)benzene, 1,8-diisocyanatooctane, 1,12-diisocyanatododecane, 4,4'-methylenebis(2,6-diethylphenyl isocyanate), trimethyl-1,6-diisocyanatohexane, 1-chloromethyl-2,4-diisocyanatobenzene, 1,5-diisocyanato-2-methylpentane, 4,4'-methylenebis(phenyl isocyanate), 2,4,6-trimethyl-1,3-phenylene diisocyanate, trans-1,4-cyclohexylene diisocyanate, isophorone diisocyanate, 4,4'-methylenebis (cyclohexyl isocyanate), 1,3-phenylene diisocyanate, tolylene-2,4-diisocyanate, 4-chloro-6-methyl-1,3-phenylene diisocyanate, hexamethylene diisocyanate.

Representative acid chlorides that can be used as linking agents directly in the polymerization reaction include but are not limited to the following: sebacoyl chloride, suberoyl chloride, succinyl chloride, isophthaloyl chloride, itaconyl chloride, dimethylmalonyl chloride, dodecanedioyl dichloride, azelaic acid dichloride.

Representative acid chlorides that can be used as linking agents directly in the polymerization reaction include but are not limited to the following: sebacoyl chloride, suberoyl chloride, succinyl chloride, isophthaloyl chloride, itaconyl chloride, dimethylmalonyl chloride, dodecanedioyl dichloride, azelaic acid dichloride.

Representative carboxylic acids that can be activated and used as linking agents in the polymerization reaction include but are not limited to the following: 1,3-acetonedicarboxylic acid, 1,3-adamantanediacetic acid, 1,3-adamantanedicarboxylic acid, phenylmalonic acid, tetrabromoterephthalic acid, azelaic acid, benzylmalonic acid, biphenyl-4,4'-dicarboxylic acid, tetrafluoroisophthalic acid, 2,2'-bipyridine-4,4'-dicarboxylic acid, 2-bromoterephthalic acid, 1,2,3,4-butanetetracarboxylic acid, 5-tert-butylisophthalic acid, butylmalonic acid, chlorosuccinic acid, 4,4'-Sulfonyldibenzoic acid, tetrafluoroterephthalic acid, 3-thiophenemalonic acid, 1,1-cyclohexanediacetic acid, trans-1,2-cyclohexanedicarboxylic acid, 1,3-cyclohexanedicarboxylic acid, terephthalic acid, 1,2,3-triazole-4,5-dicarboxylic acid, bis (carboxymethyl)trithiocarbonate, 1,3,5-cyclohexanetricarboxylic acid, 1,4,8,11-tetraazacyclotetradecane-1,4,8,11-tetraacetic acid, cis,cis-1,3,5-trimethylcyclohexane-1,3,5-tricarboxylic acid, cyclohexylsuccinic acid, trans-1,2-cyclopentanedicarboxylic acid, dibromomaleic acid, mesaconic acid, meso-2,3-dibromosuccinic acid, 4,5-dichlorophthalic acid, diethylmalonic acid, 2-methoxyisophthalic acid, 2-methoxyisophthalic acid, 6-methylpyridine-2,3-dicarboxylic acid, 3,4-dihydroxyhydrocinnamic acid, 2,5-dihydroxyterephthalic acid, 1,4-naphthalenedicarboxylic acid, 2,6-naphthalenedicarboxylic acid, 4,4'-oxybis(benzoic acid), diphenic acid, docosanedioic acid, perfluoroglutaric acid, ethylmalonic acid, 3-fluorophthalic acid, 3-fluorophthalic acid, 5-norbornenecarboxylic acid, trans-glutaconic acid, hexadecanedioic acid, 5-(octadecyloxy) isophthalic acid, 3-phenylglutaric acid, 2,2'-Iminodibenzoic acid, undecanedioic acid, 1,4-phenylenedipropionic acid.

The linking agent can also comprise a compound that contains a combination of any of the above functional groups capable of undergoing polymerization conditions with the spacer.

The polymerization conditions can also comprise a mixture of spacers and a mixture of linking agents to form a polymer containing one or more types of spacer and one or more types of linker. For example, polymerization conditions comprising a hydroxymethylaniline spacer described herein and a mixture of two or more of the linking agents listed above.

Scheme 6

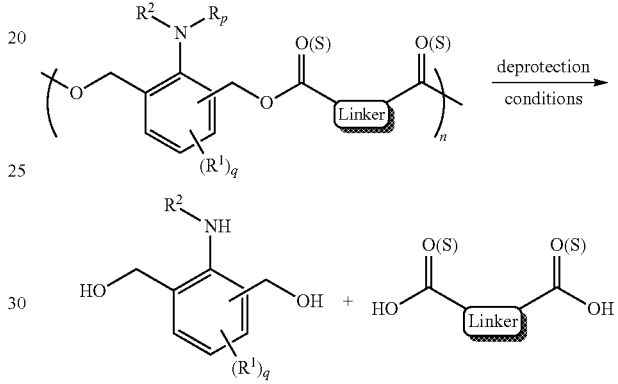

Scheme 6 shows the deprotection of aniline spacer to initiate a depolymerization event. The deprotection conditions chosen will depend of the identity of $R_P$, which may be tailored to the environment in which the polymer will be utilized. A desirable $R_P$ group will tolerate the environmental conditions in which the polymer is used, until an intended time when the deprotection of $R_P$ will trigger the depolymerization. The degradation of the polymer will produce stoichiometric amounts of the deprotected hydroxymethylaniline and the linker. Depolymerization occurs rapidly, and in some cases, depending on the linker, is driven by the evolution of gas byproducts.

Scheme 7

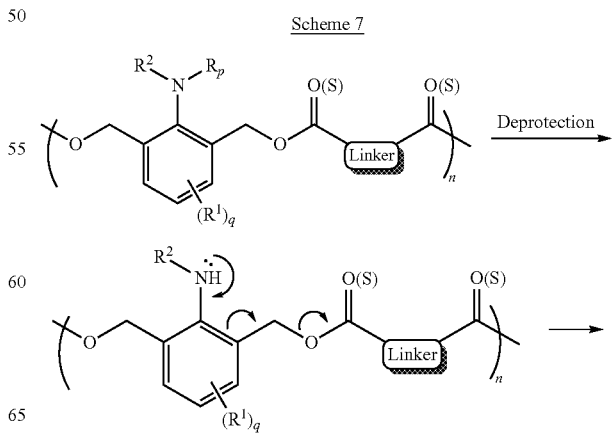

-continued

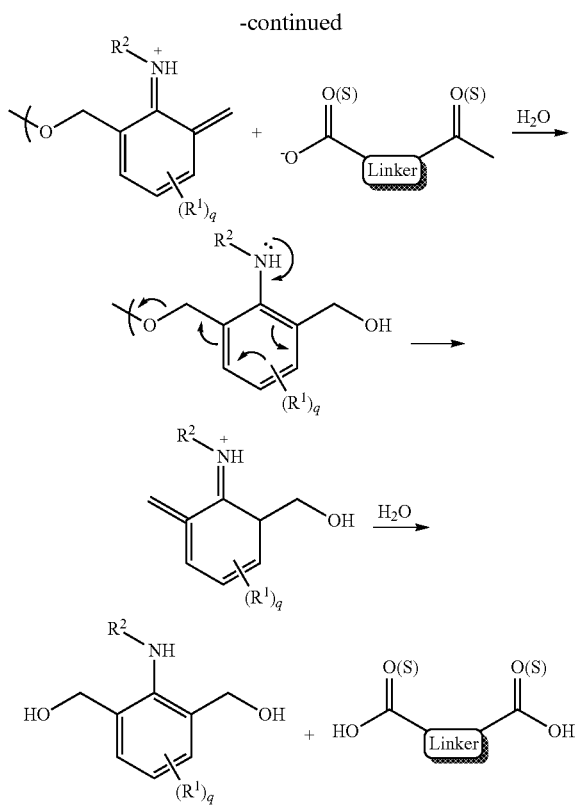

Without being bound by any particular theory of operation, a mechanism for the deprotection of particular polymers of Formula I is illustrated in Scheme 7. The electron-withdrawing nature of the nitrogen protecting group restricts the lone pair of electrons on the nitrogen atom from resonating into the benzene ring. Upon removal of the nitrogen protecting group, typically under intended deprotection conditions, the lone pair of electrons on the nitrogen becomes available. Resonance of the nitrogen electrons into the ring mediates the 1,4 elimination of the linker, and forms an azaquinonemethide, which is subsequently quenched with water. A second 1,4 elimination provides another azaquinone-methide, which is quenched with water to provide the bis(hydroxymethyl)aniline. Depending on the characteristics of the linker, further decomposition may release a gaseous byproduct.

The Examples that follow are illustrative of specific embodiments of the invention, and various uses thereof. They set forth for explanatory purposes only, and are not to be taken as limiting the invention.

EXAMPLES

Example 1

Synthesis of (2-amino-1,3-phenylene)dimethanol (2,6-bishydroxymethylaniline) (4)

To the mixture of (2-nitro-1,3-phenylene)dimethanol (5) (1.464 g, 8 mmol) and Pd/C (0.12 g, 10 w %) in MeOH (30 mL) was refluxed under $N_2$ protection for 30 min. then the hydrazine hydrate (1.25 ml, 25.8 mmol) was added slowly. The resulting mixture was stirred under reflux for another 8 h. The solid catalyst was removed by suction and the solvent was removed under reduced pressure. And the crude residue was dissolved in ethyl acetate (150 mL). The organic layer was washed with brine (3×10 mL) and dried with anhydrous $MgSO_4$, and the solvent was removed under reduced pressure. Compound 4 was obtained as a white solid (0.9 g, Yield: 63%). $^1H$ NMR (DMSO-$d_6$, 500 MHz): δ 7.01 (d, 2H, ArH), 6.51 (d, 1H, ArH), 5.03 (m, 2H, Ar—N$H_2$), 4.80 (s, 2H, OH), 4.41 (s, 4H, PhC$H_2$—OH). $^{13}C$ NMR (DMSO-$d_6$, 500 MHz): δ 143.1, 125.3, 118.6, 60.2. ESI-MS (m/z): calcd. $C_8H_{11}NO_2$ 153.1 (M). found 154.1 (M+H)$^+$. The name for compound 4 generated with ChemDraw version 10.0 is (2-amino-1,3-phenylene)dimethanol.

Example 2

Synthesis of 2-nitrobenzyl 2,6-bis(hydroxymethyl)phenylcarbamate (1a)

2-nitrobenzyl carbonochloridate (CNBZ—Cl) was prepared first. A solution of phosgene in toluene (15 mL, 20% w/w, 28.8 mmol) was added to a stirred solution of 2-nitrobenzyl alcohol (1.84 g, 12 mmol) in 20 mL of dry THF. Stirring was continued for 16 h at ambient temperature. The excess phosgene and solvents were removed under low vacuum and trapped with a NaOH aqueous solution. The yellowish oil so formed was directly used for the subsequent reaction without further purification owing to its instability.

(2-amino-1,3-phenylene)dimethanol (4) (1.50 g, 10 mmol) was dissolved in 30 mL of a mixture of THF/sat. NaHCO$_3$/water (ratio 2:2:1), followed by the addition of CNBZ—Cl (2.6 g, 12 mmol) in 6 mL dry THF by dropwise. After stirring for 1 h, the mixture was extracted with EtOAc (3×50 mL). The organic phase was washed by NaCl aqueous solution for 3 times. The organic phase was dried over Na$_2$SO$_4$ and the solvent was evaporated under vacuum. Purification by recrystallization from EtOAc gave 1a as a white crystalline (1.5 g, Yield: 45%). $^1H$ NMR (DMSO-$d_6$, 500 MHz): δ 8.88 (s, 2H), 8.16-8.09 (m, 1H), 7.83 (t, J=7.5 Hz, 1H), 7.75 (d, J=7.7 Hz, 1H), 7.63 (t, J=8.1 Hz, 1H), 7.36 (d, J=7.6 Hz, 2H), 7.31-7.24 (m, 1H), 5.44 (s, 2H), 5.10 (t, J=5.7 Hz, 2H), 4.45 (d, J=5.7 Hz, 4H). $^{13}C$ NMR (DMSO-$d_6$, 500 MHz): δ 155.6, 149.3, 134.6, 130.7, 129.6 128.5, 125.3, 124.3 61.8 60.0. ESI-MS (m/z): calcd. $C_{16}H_{16}N_2O_6$ 332.1 (M). found 333.4 (M+H)$^+$. The name for compound 1a generated with ChemDraw version 10.0 is 2-nitrobenzyl 2,6-bis(hydroxymethyl)phenylcarbamate.

Example 3

Synthesis of tert-butyl 2,6-bis(hydroxymethyl)phenylcarbamate (1b)

Under $N_2$ protection, (2-amino-1,3-phenylene)dimethanol (4) (0.65 g, 4.2 mmol) and Boc$_2$O (1.83 g, 8.4 mmol) was added into the 20 ml ethanol, and then the solution was heated to reflux for 24 h. The solvent was removed under reduce pressure, and then the solid was dissolved in ethyl acetate. The ethyl acetate was washed with saturated NaHCO$_3$ water for three times. The organic layer was dried by anhydrous Na$_2$SO$_4$ and the solvent was removed under reduced pressure. The crude product was purified by silica gel chromatography (ethyl acetate:hexane=1:1). Then the final product (1b) was obtained by crystallization from mixture of hexane and ethyl acetate as white crystalline. (0.51 g, Yield: 48%). $^1H$ NMR (DMSO-$d_6$, 500 MHz): δ 8.24 (s, 0.84H, —CO—NH—Ar—), 7.23-7.33 (m, 3H, —ArH), 5.05 (s, 2H, —CH$_2$OH), 4.4 (d, 4.1H, —CH$_2$OH), 1.43 (s, 9.2H, —C—(CH$_3$)$_3$). $^{13}C$ NMR (DMSO-$d_6$, 500

MHz): δ 154.41, 139.96, 131.77, 126.68, 125.45, 79.20, 59.88, 28.80. ESI-MS (m/z): calcd. $C_{13}H_{19}NO_4$ 253.13 (M). found 276.1 (M+Na)$^+$. The name for compound 1b generated with ChemDraw version 10.0 is tert-butyl 2,6-bis(hydroxymethyl)phenylcarbamate.

Example 4

Synthesis of (9H-fluoren-9-yl)methyl 2,6-bis(hydroxymethyl)phenyl carbamate (1c)

The Fmoc-Cl (0.6 g, 2.4 mmol) in 1,4-dixoane (20 mL) solution was added into a solution of (2-amino-1,3-phenylene)dimethanol (4) (0.352 g, 2 mmol) in 10% AcOH aqueous solution (20 mL). Then the mixture was stirred for overnight. The white precipitate was formed and collected by suction. Then the solid was washed with water three times. The crude product was recrystallized from ethanol an provided 1c as a the white solid. (0.33 g, Yield: 44%). $^1$H NMR (DMSO-d$_6$, 500 MHz): δ 8.75 (s, 1H, —CO—NH—Ar—), 7.6-7.93 (m, 11H, ArH), 5.08 (s, 2H, —CH$_2$OH), 4.3-4.43 (m, 7.5H, —CH—CH$_2$—, —CH$_2$OH). $^{13}$C NMR (DMSO-d$_6$, 500 MHz): δ 196.85, 154.99, 144.46, 141.48, 140.13, 131.26, 128.38, 127.81, 127.01, 125.87, 125.48, 121.61, 120.87, 96.18, 66.27, 59.76, 47.50, 40.70, 40.53, 40.36, 40.29, 40.20, 40.12, 40.03, 39.86, 39.70. ESI-MS (m/z): calcd. $C_{23}H_{21}NO_4$ 375.15 (M). found 398.1 (M+Na)$^+$. The name for compound 1c generated with ChemDraw version 10.0 is (9H-fluoren-9-yl)methyl 2,6-bis(hydroxymethyl)phenyl carbamate.

Example 5

Synthesis of 4-(4,4,5,5-tetramethyl-1,3,2-dioxaborolan-2-yl)benzyl 2,6-bis(hydroxymethyl)phenylcarbamate (1d)

Compound 4 (0.61 g, 4 mmol) in THF (15 mL) was added to an ice bath cooled suspension of sodium hydride (0.23 g, 8.8 mmol, 1.1 equiv.) in THF (10 mL). The reaction mixture was stirred for 15 min followed by dropwise addition of TBDMS-Cl (1.45 g, 9.6 mmol, 1.2 equiv.) in THF (5 mL). The reaction solution was allowed to gradually warm to room temperature and stirred overnight. The reaction mixture was poured into a brine solution (100 mL) and extracted with EtOAc (3×50 mL). The organic phase was dried with anhydrous Na$_2$SO$_4$ and the solvent was evaporated under vacuum to provide 2,6-bis((tert-butyldimethylsilyloxy)methyl)aniline as a colorless oil, which was used directly without purification (1.43 g, yield 94%).

To a dried flask, phosgene (20% in toluene, 20 mL, 38 mmol) was added under nitrogen followed by dropwise addition of 2,6-bis((tert-butyldimethylsilyloxy)methyl)aniline (1.43 g, 3.75 mmol) in 10 mL of toluene. The reaction mixture was stirred for 30 min at reflux and monitored by TLC. After 1 h, the solvent was removed under reduced pressure. 4-(Hydroxymethyl)phenylboronic acid pinacol ester (1.0 g, 4.4 mmol) in toluene (10 mL) was added, followed by DBTL (100 μL, 0.163 mmol). The reaction mixture was heated to reflux (110° C.) for 1 h. The solvent was removed under reduced pressure. The crude product was purified by silica gel column chromatography (EtOAc/Hex, 1:6) to give 4-(4,4,5,5-tetramethyl-1,3,2-dioxaborolan-2-yl)benzyl 2,6-bis((tert-butyldimethylsilyloxy)methyl)phenylcarbamate (1.5 g, yield 60%) as a white solid. $^1$H NMR (CDCl$_3$, 500 MHz): _ 7.83 (d, J=7.8 Hz, 2H, B—Ar—H), 7.38 (dd, J=7.8 Hz, 2H, OCH$_2$—Ar—H), 7.30-7.19 (m, 3H, CONH—Ar—H), 5.22 (s, 2H, NHCOO—CH$_2$-Ph), 4.70 (s, 4H, SiO—CH$_2$-Ph), 1.37 (s, 12H, (CH$_3$)$_2$—CC—(CH$_3$)$_2$), 1.02-0.84 (m, 18H, (CH$_3$)$_3$—CSi), 0.09 (s, 12H, (CH$_3$)$_2$—Si). ESI-MS (low resolution, positive mode): calculated for $C_{34}H_{57}BNO_6Si_2$, m/z, 642.3 [M+H]+. found 642.3 [M+H]+.

4-(4,4,5,5-tetramethyl-1,3,2-dioxaborolan-2-yl)benzyl 2,6-bis((tert-butyldimethylsilyloxy)methyl)phenylcarbamate (500 mg, 0.8 mmol) was dissolved in a mixture of TFA and DCM (1:1, v/v, 6 mL), and stirred for 25 min. The solvents were then removed under reduced pressure. The crude product was purified by silica gel column chromatography (EtOAc/Hex, 1:1) to give compound 1d (250 mg, yield 77%) as a white solid. 1H NMR (DMSO-d6, 500 MHz): _ 7.71 (d, J=7.6 Hz, 2H, B—Ar—H), 7.45-7.25 (m, 5H, OCH$_2$—Ar—H and CONH—Ar—H), 5.18-5.06 (m, 3H, NHCOOCH$_2$-Ph and CONH), 4.46 (s, 4H, Ph-CH$_2$—OH), 1.30 (s, 12H, (CH$_3$)$_2$—CC—(CH$_3$)$_2$). 13C NMR (DMSO-d6, 500 MHz): d 156.6, 148.2, 135.6, 133.5, 130.7, 128.6 126.5, 124.3, 88.9, 67.2, 60.0, 25.3. ESI-MS (low resolution, positive mode): calculated for $C_{22}H_{29}BNO_6$, m/z, 414.3 [M+H]+. found 414.4 [M+H]+.

Example 6

Synthesis of Poly(1a/2)

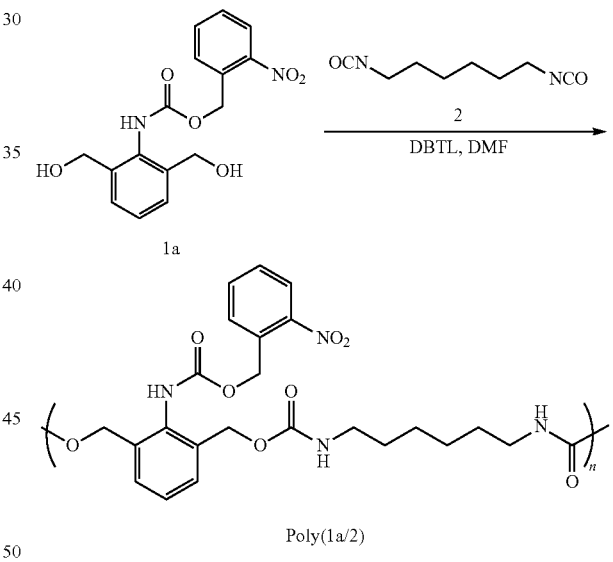

Poly(1a/2)

Under N$_2$ atmosphere, 2-nitrobenzyl 2,6-bis(hydroxymethyl)phenylcarbamate (1a) (99.3 mg, 0.3 mmol), hexamethylene diisocyanate (2) (50.3 mg, 0.3 mmol), 5 μL of DBTL, and 3 mL of dry DMF were added into a Schlenk tube. The solution was degassed under low pressure for 1 min and sealed under low pressure. Then the reaction was stirred at 80° C. for 16 h. The solution was diluted to 10 g/L to do the GPC test. And the polymer was by precipitated and centrifuged from ether. Yield: 58% (white solid). $M_w$=6.9 kDa; $M_w/M_n$=1.48 (determined by gel-permeation chromatography (GPC) relative to polystyrene standards). $^1$H NMR (DMSO-d$_6$, 500 MHz): δ 8.13 (d, 1H, ArH), 7.81-7.61 (m, 2H, ArH) 7.25-7.00 (m, 4H, ArH), 5.70 (s, —CONH—Ar), 5.47 (s, 2H, -PhCH$_2$O—CO—), 4.99 (s, 4H, -PhCH$_2$O—CO—), 2.94 (m, 4H, —NH—CH$_2$—CH$_2$—), 1.06-1.44 (br, m, 8H, —NH—CH$_2$—CH$_2$—CH$_2$—).

Example 7

Synthesis of Poly(1a/3)

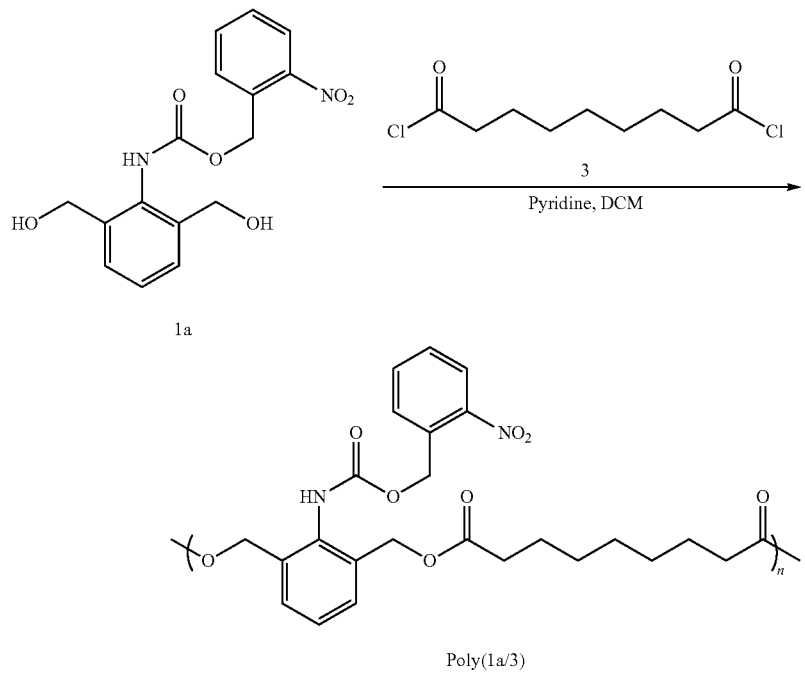

Poly(1a/3)

2-nitrobenzyl 2,6-bis(hydroxymethyl)phenylcarbamate (1a) (166 mg, 0.5 mmol) and azelaic acid dichloride (99 μL, 0.5 mmol) were dissolved in 2 mL dry DCM under nitrogen, and pyridine (200 μL, 2.5 mmol) was added to the reaction mixture dropwise over 3 min. The polymerization was allowed to proceed for 16 h at room temperature. The reaction mixture was concentrated to 0.5 mL and precipitated into 20 mL of cold EtOH, yielding yellow polymer. The oligomers were removed by repeated precipitation of the polymer into cold EtOH. Yield: 68% (white solid). $M_w$=13.8 kDa; $M_w/M_n$=1.46 (determined by gel-permeation chromatography (GPC) relative to polystyrene standards). $^1$H NMR (DMSO-$d_6$, 500 MHz): δ 9.30 (s, —CONH—Ar), 8.11 (d, 1H, ArH), 7.81-7.59 (m, 3H, ArH) 7.35-7.20 (m, 3H, ArH), 5.45 (s, 2H, -PhCH$_2$O—CO—), 5.05 (s, 4H, -PhCH$_2$O—CO—), 2.26 (m, 4H, —OCO—CH$_2$—CH$_2$—), 1.45 (m, 4H, —OCO—CH$_2$—CH$_2$—), 1.17 (br, m, 8H, —OCO—CH$_2$—CH$_2$—CH$_2$—).

Example 8

Synthesis of Poly(1b/2)

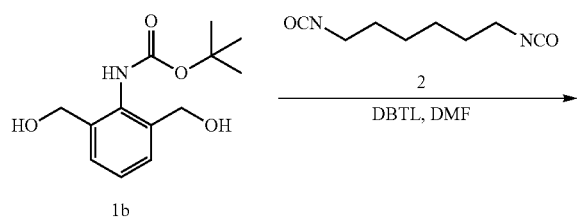

-continued

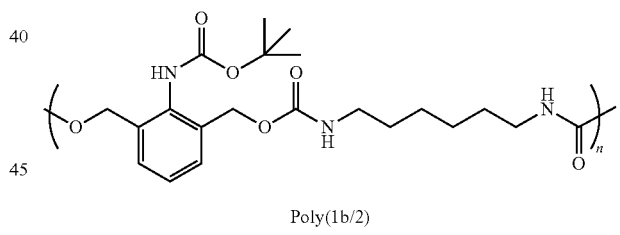

Poly(1b/2)

Under N$_2$ atmosphere, tert-butyl 2,6-bis(hydroxymethyl)phenylcarbamate (1b) (0.253 g, 1 mmol), hexamethylene diisocyanate (2) (0.168 g, 1 mmol), 20 μL of DBTL, and 8 mL of dry DMF were added into a Schlenk tube. The solution was degassed under low pressure for 1 min and sealed under low pressure. Then the reaction was stirred at 80° C. for 20 h. Then the polymer was by precipitated and centrifuged from ether. 0.21 g of white solid was obtained (Yield: 50%). $M_n$=10.9 kDa; $M_w/M_n$=1.3. $^1$H NMR (DMSO-$d_6$, 500 MHz): δ 8.64 (s, (CH$_3$)$_3$C—O—CO—NH—Ar), 7.29 (m, 5H, ArH, —CO—NH—CH$_2$—), 4.97 (d, 2H, —CH$_2$O—CO—), 2.96 (m, 4H, —NH—CH$_2$—), 1.23-1.44 (br, m, 17H, —NH—CH$_2$—CH$_2$—CH$_2$— and (CH$_3$)$_3$C—).

Example 9

Synthesis of Poly(1c/2)

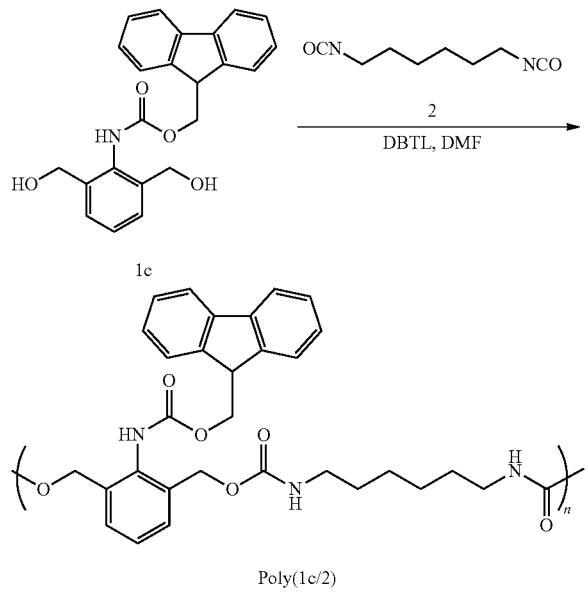

Under N$_2$ atmosphere, (9H-fluoren-9-yl)methyl 2,6-bis(hydroxymethyl)phenyl carbamate (1c) (0.1875 g, 0.5 mmol), hexamethylene diisocyanate (2) (0.084 g g, 0.5 mmol), 5 μL of DBTL, and 4 mL of dry DMF were added into a Schlenk tube. The solution was degassed under low pressure for 1 min and sealed under low pressure. Then the reaction was stirred at 80° C. for 20 h. Then the polymer was by precipitated and centrifuged from ether. 0.13 g of white solid was obtained (Yield: 70%). $M_n$=15.6 kDa; $M_w/M_n$=1.56 $^1$H NMR (DMSO-d$_6$, 500 MHz): δ 9.1 (s, 1H, —CO—NH—Ar—), 7.0-7.93 (m, 11H, ArH and —Ar—CH$_2$—OCO—NH—), 4.9 (d, 2H, —Ar—CH$_2$O—), 4.3-4.43 (m, 7.5H, >CH—CH$_2$—, —CH$_2$OH), 2.95 (m, 4H, —NH—CH$_2$—), 1.21-1.38 (br, m, 8H, —NH—CH$_2$—CH$_2$—CH$_2$—).

Example 10

General Procedure for the Photolysis of Polymers and GPC Analysis

A 10 mg/mL solution of the polymer to be analyzed in DMF/water (95/5 v/v) was transferred to a quartz cuvette. The cuvette was placed inside a photoreactor (365 nm, 40 mW/cm$^2$) and irradiated for the specified periods of time. The analyzed solution was directly used for GPC analysis. See Table 1 and FIG. 1.

TABLE 1

Photolysis of polymers poly(1a/2) and poly(1a/3)

| Entry | Polymer | Time (min) | Mn (kDa) | MWD |
|---|---|---|---|---|
| 1 | poly(1a/2) | 0 | 6.9 | 1.48 |
| 2 | poly(1a/2) | 60 | 2.8 | 2.68 |
| 3 | poly(1a/2) | 120 | 1.8 | 3.26 |

TABLE 1-continued

Photolysis of polymers poly(1a/2) and poly(1a/3)

| Entry | Polymer | Time (min) | Mn (kDa) | MWD |
|---|---|---|---|---|
| 4 | poly(1a/3) | 0 | 13.8 | 1.46 |
| 5 | poly(1a/3) | 10 | 7.5 | 2.35 |
| 6 | poly(1a/3) | 30 | 1.9 | 2.86 |

Example 11

General Procedure for the Hydrolysis of Polymers Using Acid or Base Condition and GPC Analysis Acid condition hydrolysis: A 10 mg/mL solution of polymer in TFA/CH$_2$Cl$_2$ (v/v=1:1) was treated for the specified amount of time. The solvent was removed under vacuum and the resulting residue was dissolved in 1 ml DMF for GPC analysis. See Table 2 and FIG. 1.

Base condition hydrolysis: A 10 mg/ml solution of polymer in various ratios of piperidine/DMF (piperidine/DMF (v/v)=5:95, 10:90, 20:80) was treated for the specified amount of time. The resulting solution was directly in the GPC analysis. See Table 2 and FIG. 1.

TABLE 2

Acid/Base degradation of polymers poly(1b/2) and poly(1c/2)

| Entry | Polymer | Condition | Time (min) | Mn (kDa) | MWD |
|---|---|---|---|---|---|
| 1 | poly(1b/2) | TFA | 0 | 10.9 | 1.36 |
| 2 | poly(1b/2) | TFA | 480 | 7.7 | 1.59 |
| 3 | poly(1c/2) | Piperidine | 0 | 15.6 | 1.56 |
| 4 | poly(1c/2) | Piperidine | 360 | 7.26 | 2.65 |

Example 12

General Procedure for the Preparation of Nile Red Encapsulated Nanoparticles and UV-Mediated Release of the Nile Red from Nanoparticles The polymer (poly(1a/3)) (7.5 mg) and Nile Red (0.5 mg) were dissolved in 1 mL DCM, and the solution was added to 15 mL of PBS (pH 7.4) containing 1% PVA. The mixture was stirred at 1000 rpm for 10 min to prepare an emulsion. The nanocapsule suspension was stirred at 1000 rpm using a magnetic stirrer to evaporate the DCM. Unencapsulated Nile Red was removed by filtering the suspension through 1 micron Glassfiber Prefilter (Millipore). A concentrated mode tangential flow filtration system using 500 kDa Pellicon XL cassette (Millipore, USA) was used to remove the PVA. The suspension was lyophilized and stored as a solid. The encapsulation efficiency was determined to be 9%.

Figure 2:
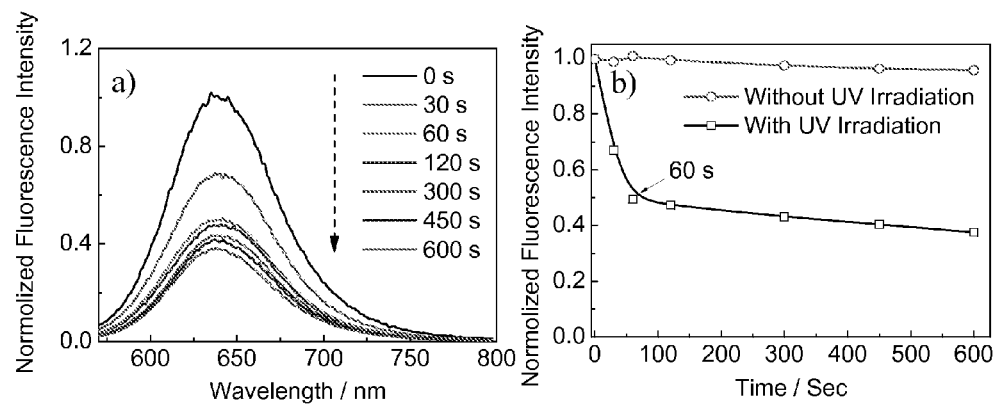
FIG. 2 shows (a) normalized fluorescence emission spectra; and (b) fluorescence intensity of Nile Red encapsulated in poly(1a/3) nanoparticles before and after irradiation (365 nm, 40 mW/cm$^2$; monitored at 634 nm, excitation at 556 nm).
Figure 2A:
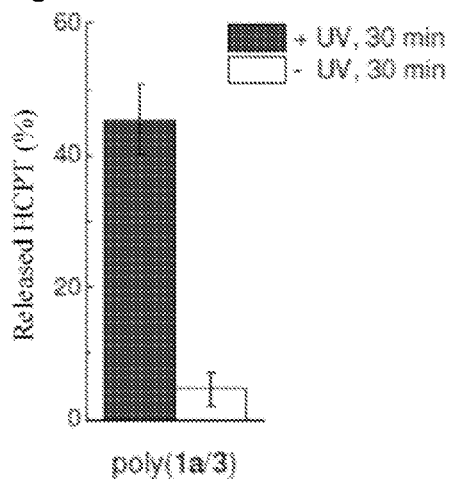
FIG. 2A shows the release of camptothecin (CPT) from poly(1a/3) based nanoparticles treated with UV (in PBS, 365 nm, 20 mW/cm$^2$) for 30 min or without UV treatment.

The aqueous solution of Nile red encapsulated nanoparticle of poly(1a/3) in a quartz cuvette was placed inside a photoreactor and irradiated for the specified periods of time. (Em: 634 nm; Ex 556 nm). See FIG. 2a/b.

Example 13

Procedure for the Preparation of Camptothecin (CPT) Encapsulated Nanoparticles and UV-Mediated Release of the Camptothecin (CPT) from Nanoparticles A DMSO solution (1 mL) of poly(1a/3) (10 mg), PEG-b-PLLA (10 mg) and camptothecin (CPT) (1 mg) was added to a rapidly stirred PBS solution (pH 7.4, 9 mL, 1300 rpm). The mixture was stirred for another 15 min at room temperature. Free CPT was removed by centrifugation (1,000 rpm for 10 min). The loading of CPT in poly(1a/3)/PEG-b-PLLA nanoparticles was 3.2% based on HPLC analysis. The loading efficiency of CPT in poly(1a/3)/PEG-b-PLLA nanoparticles was determined to be 64%. The CPT-encapsulated nanoparticles in water were placed in a quartz cuvette at a concentration of 0.2 mg/mL and treated with UV for a specified period of time. After UV treatment, the nanoparticle solution was stirred for predefined periods of time at room temperature. The solution was centrifuged for 15 min at 15,000 rpm and the upper layer was used for HPLC analysis to determining the released CPT. See FIG. 2a.

and the filtrate was washed with water twice. The organic layer phase was dried with $Na_2SO_4$ and crude product was obtained after removal of solvent and was further purified by silica gel silica gel chromatography (ethyl acetate:hexane=2: 1). Yield (60%) $^1$H NMR (500 MHz, $CDCl_3$) δ 8.22-7.89 (m, 22H), 7.77-7.63 (m, 4H), 7.58 (d, J=8.0 Hz, 1H), 7.52 (s, 2H), 7.47-7.36 (m, 3H), 7.35-7.20 (m, 6H), 5.55 (s, 3H), 5.18-5.08 (m, 6H), 3.33-3.17 (m, 6H), 2.47-2.34 (m, 5H), 2.19-2.09 (m, 5H). $^{13}$C NMR (500 MHz, $CDCl_3$) δ 225.20, 188.81, 186.52, 170.51, 168.26, 165.93, 154.35, 149.89, 135.65, 133.92, 131.05, 130.54, 129.44, 128.80, 127.58, 126.93, 126.05, 125.19, 124.97, 123.40, 33.95, 32.80, 26.87. MALDI-MS: cal. 872.3. found 872.3 ([M]+), 895.3 ([M+Na]+).

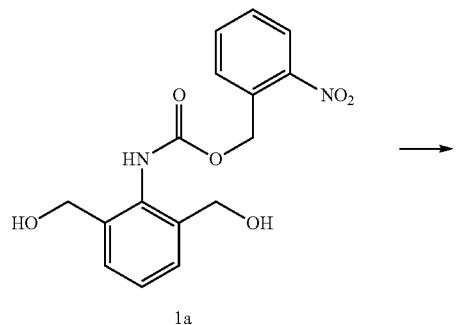

1a

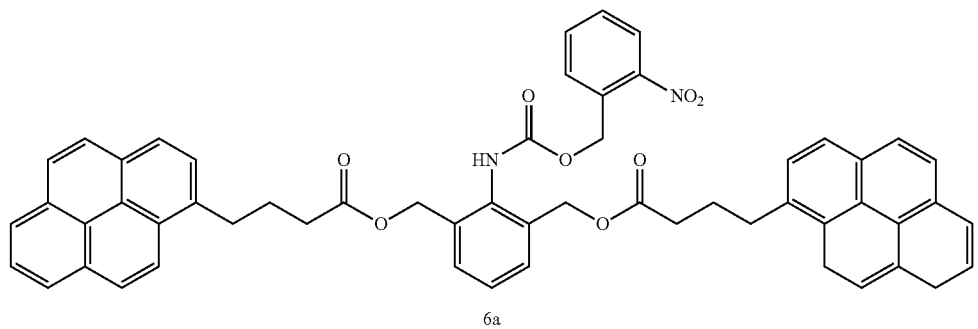

6a

Example 14

Synthesis of Compound 6a 1-pyrenebutyric acid (288 mg, 1 mmol) was dissolved in 5 mL dry DCM and 1.5 mL $SOCl_2$ was added (cat. 20 mmol). The resulting solution was heated to reflux for 3 h and the solvent was removed under vacuum. The 1-pyrenebutyric chloride as resulting liquid was obtained and used directly. Then 5 mL DCM was added to dissolve the 1-pyrenebutyric chloride. Compound 1a (100 mg, 0.3 mmol) was dissolved in 16 mL DCM/THF (v/v=1:3) and the solution was added into above solution, followed with addition of pyridine (80 μL, 1 mmol). The reaction was stirred under r.t overnight. The resulting solution was filtered

Example 15

UV Irradiation and HPLC Analysis of 6a

Figure 3C:
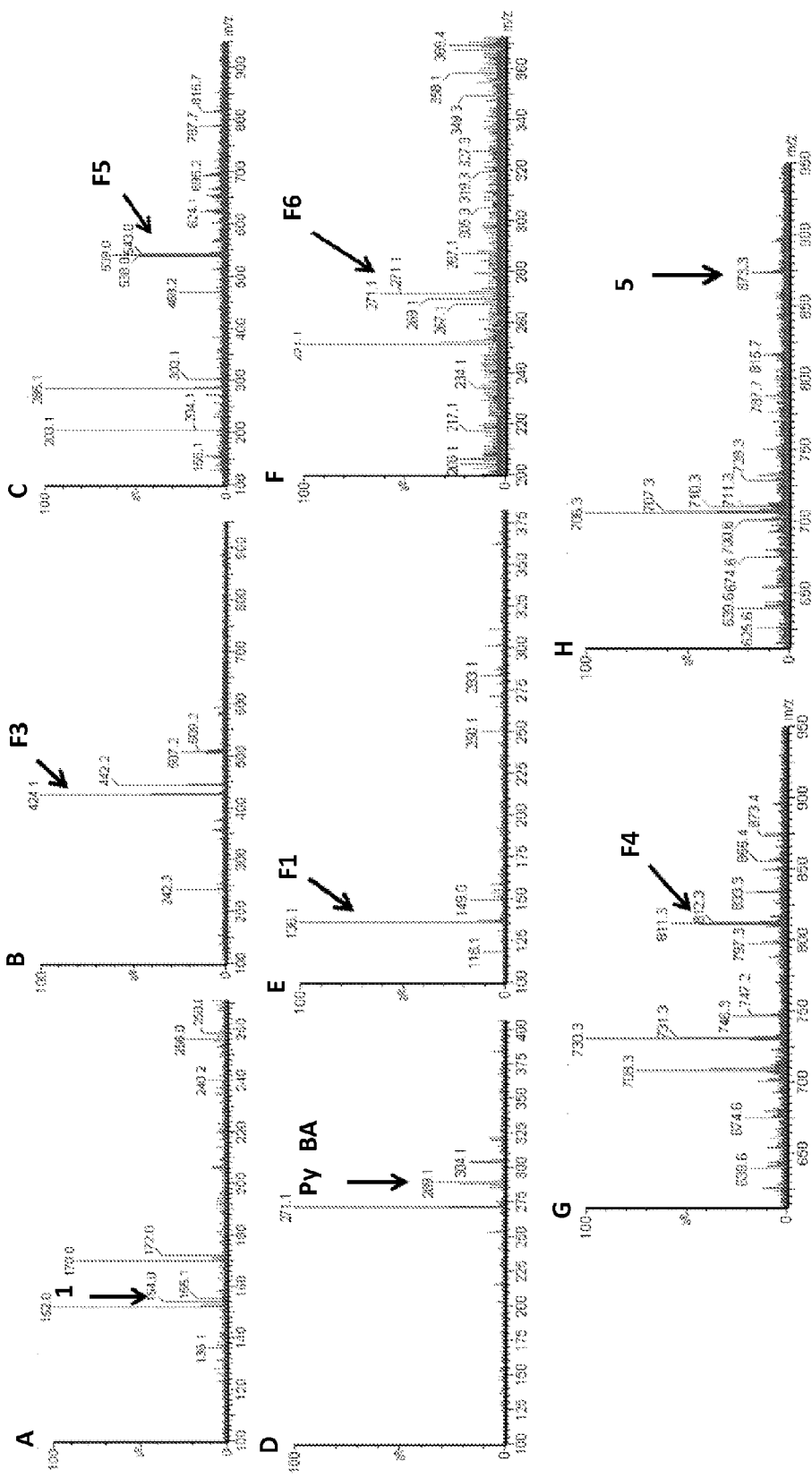
FIG. 3 shows (a) the suggested mechanism for UV-mediated disassembly of 2,6-bis(hydroxymethyl)aniline-based model compound 6a; (b) HPLC chromatogram after UV irradiation of a 0.1 mg/mL solution of 6a in 9:1 (v/v) acetonitrile/water (50 mW/cm$^2$, 45 min); (c) ESI-MS spectra of fragments obtained by HPLC separation (the fragments labeled A-H correspond to peaks A-H in FIG. 3b; compound labels correspond to those in FIG. 3a); and (d) the release of 1-pyrenebutyric acid from 6a after UV treatment (0.1 mg/mL solution in 9:1 (v/v) ACN/water, 50 mW/cm$^2$).
Figure 3D:
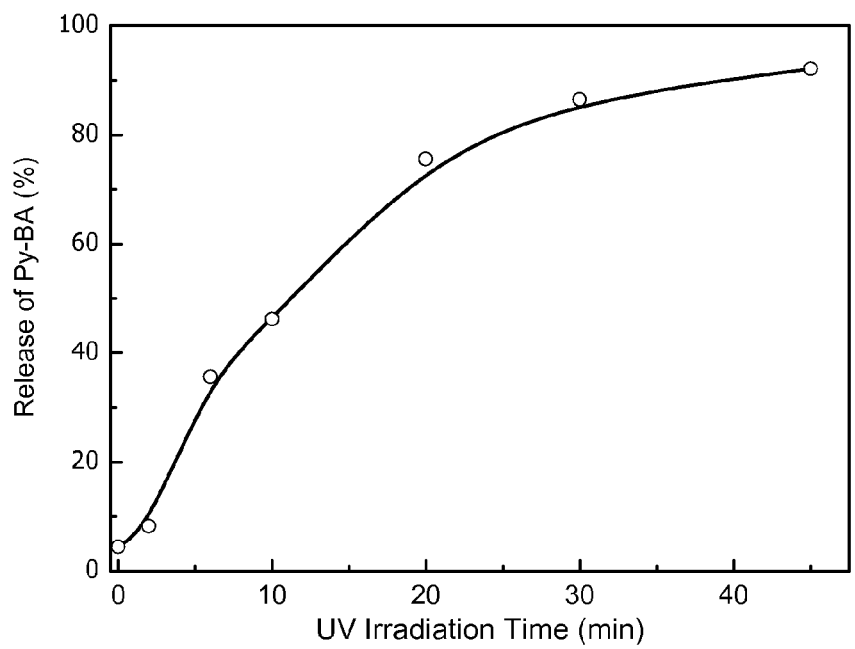

Analysis of a solution of 6a in 9:1 (v/v) acetonitrile/water by LC-MS after UV irradiation indicated that 1-pyrenebutyric acid was the major degradation product. We also identified other fragments of 6a and F1-F6 (see the chemical structures in FIG. 3a,c), which confirmed the proposed degradation mechanism (FIG. 3a). HPLC analysis of the kinetics of 1-pyrenebutyric acid release from 6a in 9:1 acetonitrile/water indicated that more than 90% of the 1-pyrenebutyric acid was recovered after UV irradiation for 45 min (FIG. 3d).

Example 16

Synthesis of CPT/1a/CPT

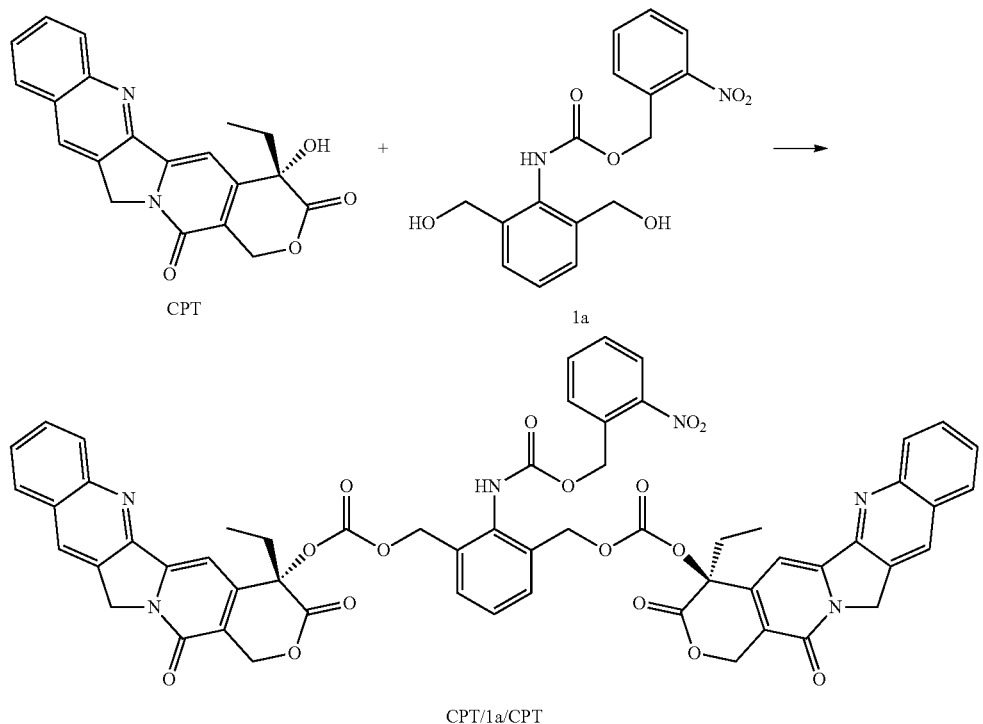

Under $N_2$ atmosphere, camptothecin (CPT) (70 mg, 0.2 mmol) and triphosgene (22 mg, 0.067 mmol) were dispersed in DCM (10 mL). Then DMAP (78 mg, 0.64 mmol) was added. Then the mixture was stirred at R.T. for 15 min. 2,6-bis(hydroxymethyl)phenylcarbamate (1a) (20 mg, 0.06 mmol) was added. Then the solution was stirred at R.T. for overnight. The solution was diluted with 50 mL of DCM and washed with HCl aqueous solution and water. The organic phase was dried with $Na_2SO_4$. The solvent was removed by evaporator. The residues was purified by pre-HPLC (EtOAc/iPA) to give the slight yellow solid (35 mg, 53%). $^1$H-NMR (CDCl$_3$, 500 MHz): δ 8.37 (s, 1H), 8.24 (d, J=8.5 Hz, 1H), 7.98-7.91 (m, 1H), 7.85 (ddd, J=8.4, 6.9, 1.4 Hz, 1H), 7.69 (ddd, J=8.2, 6.8, 1.2 Hz, 1H), 7.57-7.48 (m, 1H), 7.48-7.28 (m, 4H), 5.72 (d, J=17.1 Hz, 1H), 5.40 (d, J=17.1 Hz, 1H), 5.38-5.22 (m, 2H), 5.21-5.09 (m, 3H), 2.30 (dq, J=15.5, 8.1, 7.7 Hz, 1H), 2.18 (dq, J=14.5, 7.3 Hz, 1H), 1.04 (t, J=7.6 Hz, 3H).

Example 17

HPLC of CPT/1a/CPT During UV Treatment

Figure 4:
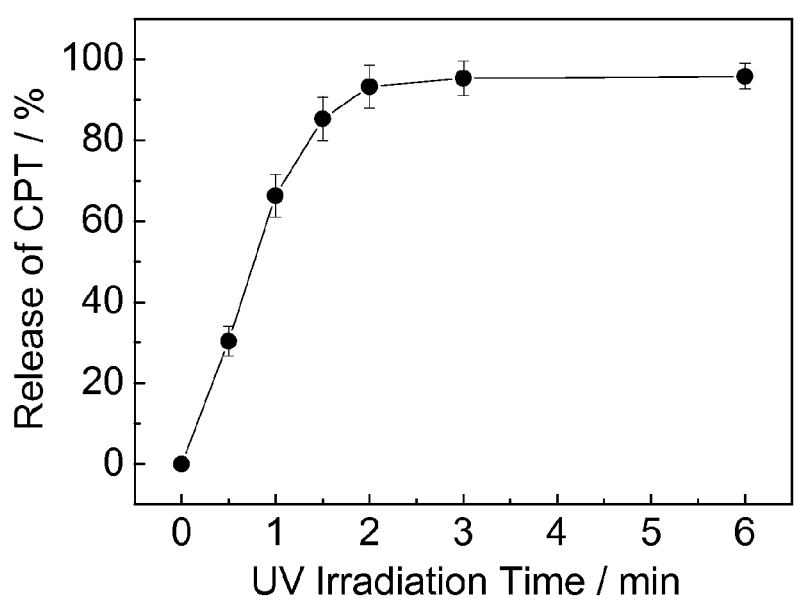
FIG. 4 shows the release of camptothecin (CPT) from CPT/1a/CPT with UV treatment (0.1 mg/mL in ACN/water (9/1 v/v) solution, exposure to 50 mW/cm$^2$).
Figure 5:
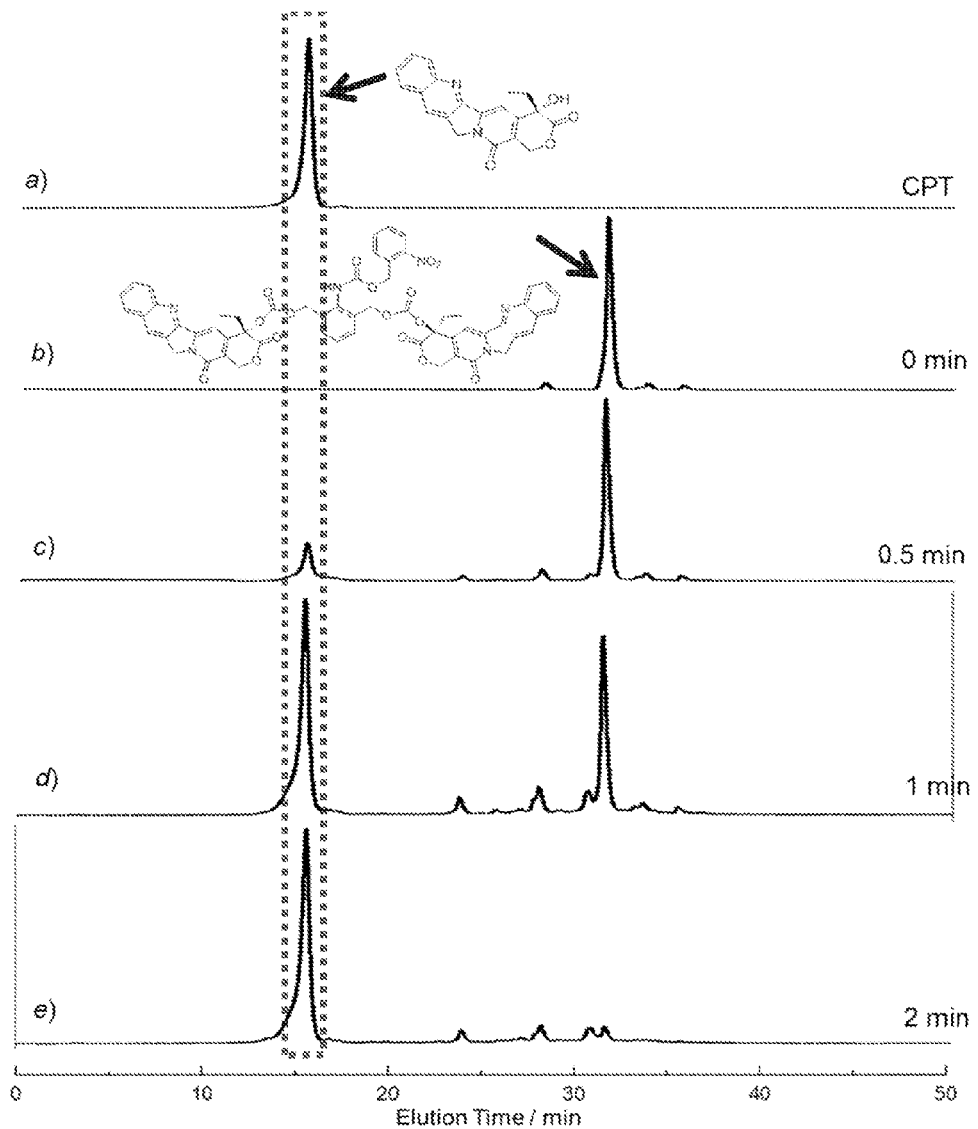
FIG. 5 shows HPLC curves of (a) CPT before treatment; (b) CPT/1a/CPT before treatment; and (c-e) CPT/1a/CPT after UV treatment (0.15 mg/mL in ACN/water (9/1 v/v) solution, exposure to 50 mW/cm$^2$).

A solution of CPT/1a/CPT (0.2 mg/mL, 9:1 ACN/H$_2$O) in a quartz cuvette was placed inside a photoreactor and irradiated for the specified periods of time. The solution was centrifuged (15000 rpm for 15 min) and the resulting suspension was used for HPLC tests. See FIGS. 4 and 5.

Example 18

Synthesis of 10-Hydroxycamptothecin Polymer Poly(HCPT/1a)

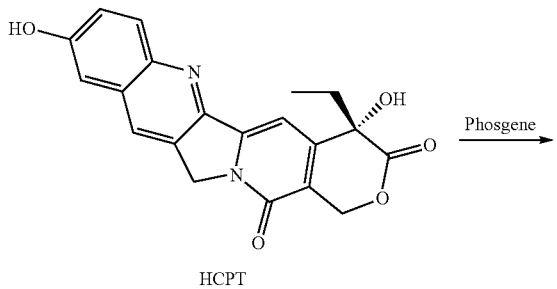

-continued

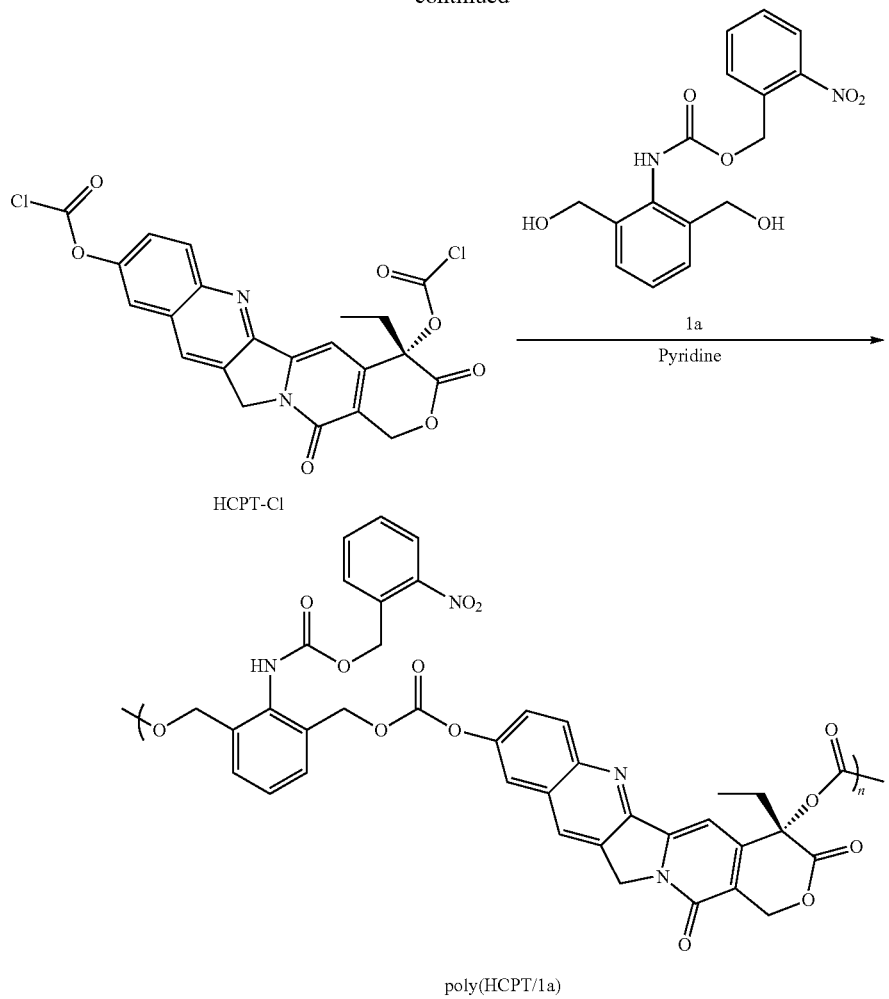

HCPT-Cl poly(HCPT/1a)

Under N₂ atmosphere, 10-hydroxycamptothecin (HCPT) (50 mg, 0.132 mmol) was dispersed in a solution of 20% phosgene in toluene (2 mL, 3.8 mmol) and DCM (2 mL). The mixture was stirred for overnight at room temperature. Then, the solvent was removed under reduced pressure, and keep in the vacuum for additional 2 h. Then, 6 mL of dry DCM was added to dissolve the solid. 2,6-bis(hydroxymethyl)phenylcarbamate (1a) (44 mg, 0.132 mmol) and pyridine (100 uL) were added. Then the solution was stirred for 24 hours at room temperature, some precipitations were formed during polymerization. Then, the mixture was added into 30 mL ether to get precipitation. The precipitation was wash with methanol for 3 times to remove the pyridine and others. The slight yellow solid, poly(CPT/1a), was obtained by dried under vacuum. Yield: 49%. $M_w$=9.1 kDa; PDI=1.45 (determined by gel-permeation chromatography (GPC) relative to polystyrene standards).

Example 19

Synthesis of 9-Aminocamptothecin Polymers Poly(ACPT/1a) and Poly(ACPT/1d)

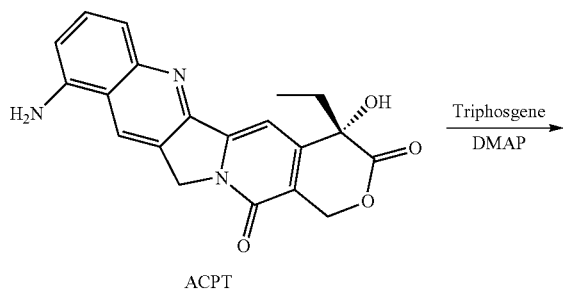

ACPT

-continued

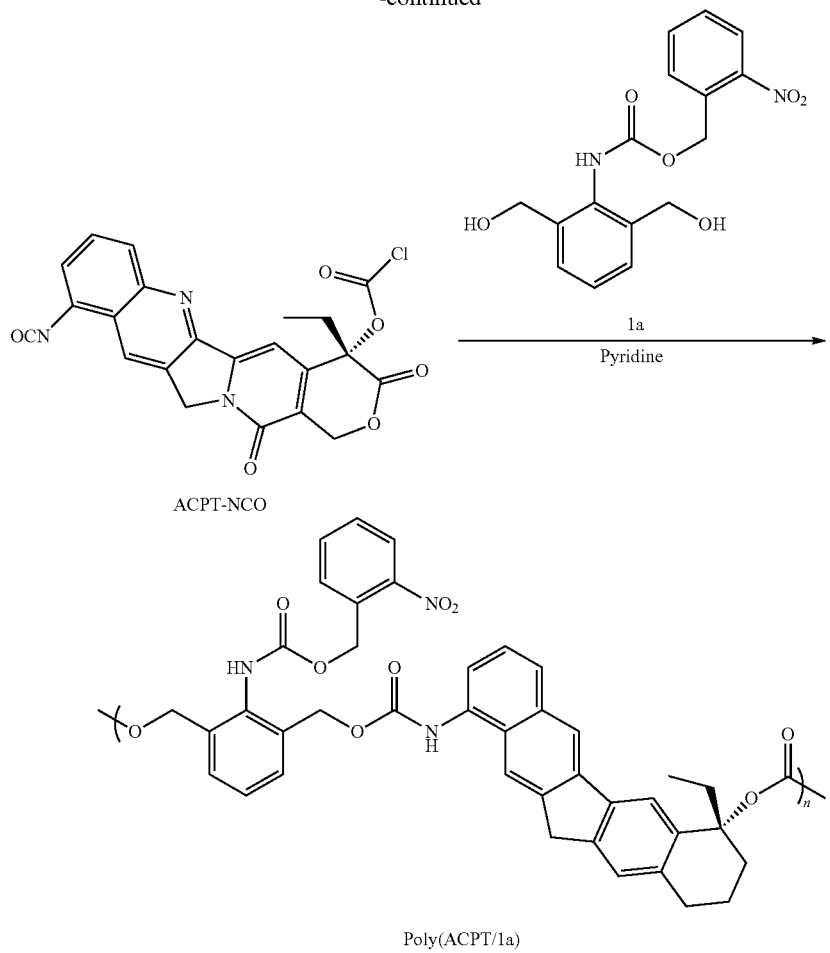

Poly(ACPT/1a)

9-Aminocamptothecin (ACPT) (36 mg, 0.1 mmol) and triphosgene (22 mg, 0.067 mmol) were dispersed in dry DCM (15 mL) under nitrogen. DMAP (78 mg, 0.64 mmol) was added to the mixture, and the mixture was stirred for 15 min, followed by addition of 1a (33 mg, 0.1 mmol). The solution was stirred for 24 h at room temperature and poured into ethyl ether (30 mL). The precipitation was collected by centrifugation, washed with methanol (3×20 mL) to remove DMAP and other low MW materials, and dried under vacuum. Poly(ACPT/1a) was obtained as a slight yellow solid (yield 33%). Mn=4.8 kDa; PDI=1.50.

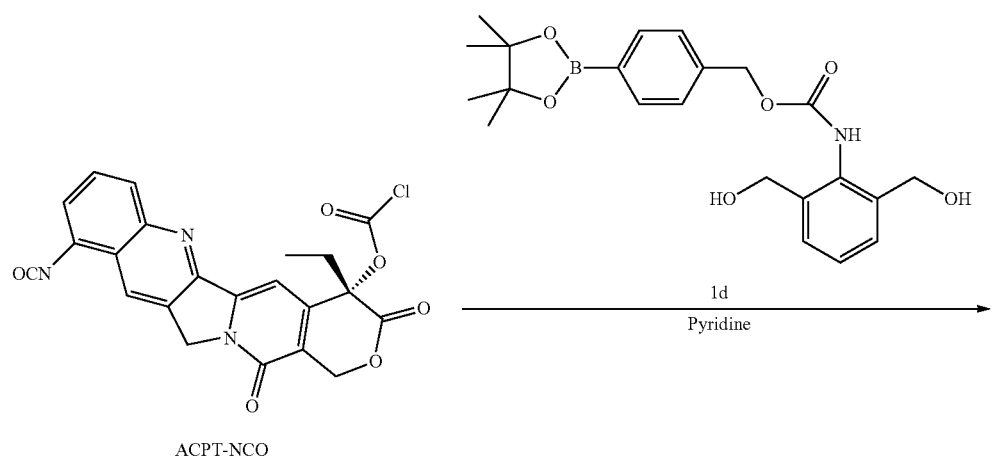

-continued

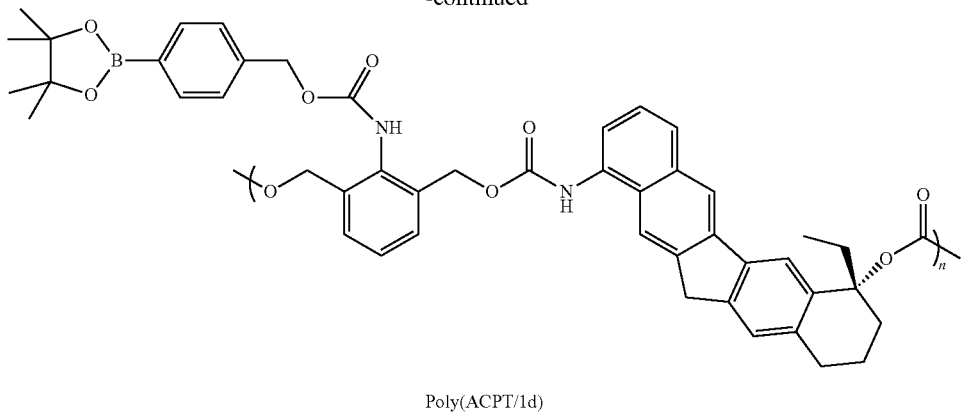

Poly(ACPT/1d)

Poly(ACPT/1d) was synthesized according to the procedure used to synthesize poly(ACPT/1a), but replacing diol 1a with 1d. Poly(ACPT/1d) was obtained as a slight yellow solid (yield 39%). Mn=5.2 kDa; PDI=1.52.

Example 20

General Procedure for the UV-Mediated Release of Camptothecin (CPT) Polymers

Figure 6:
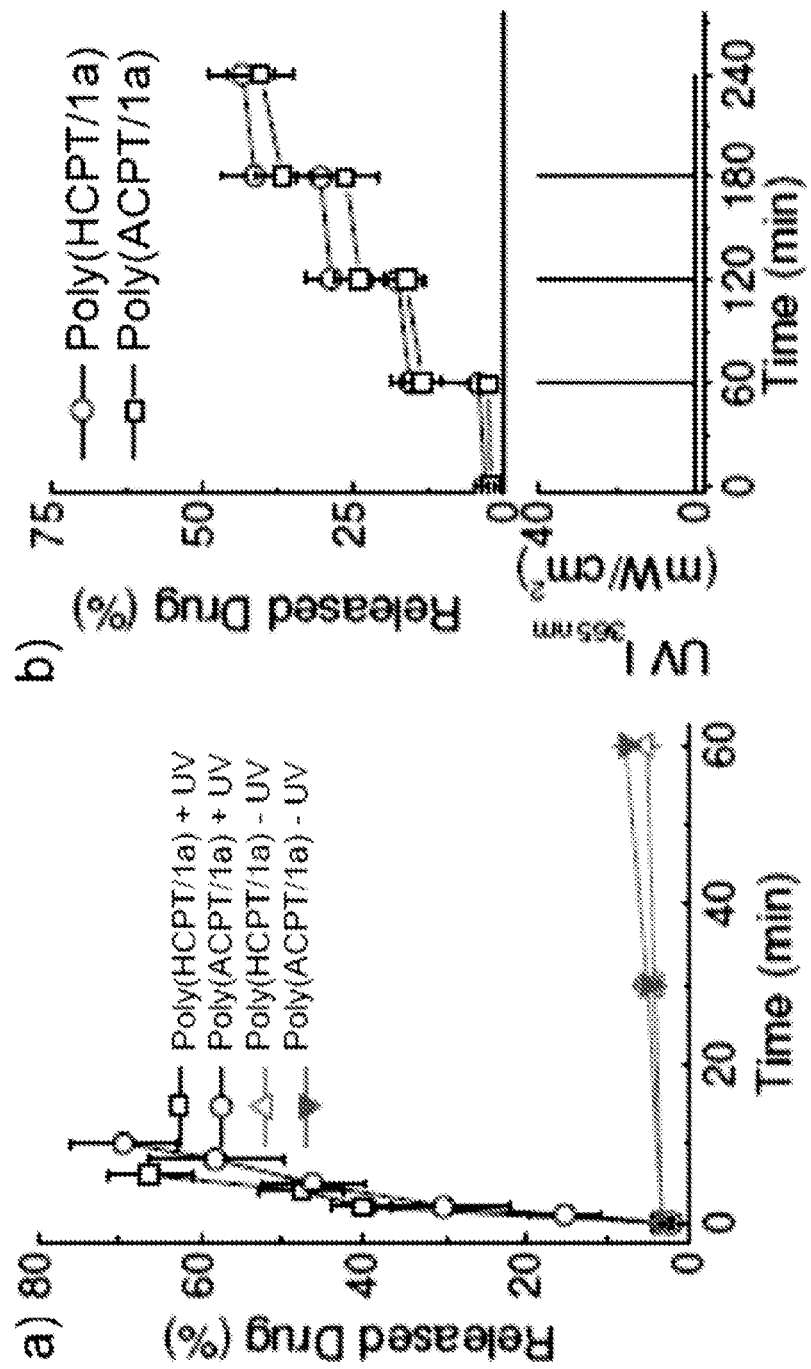
FIG. 6 shows a) release of 10-hydroxycamptothecin (HCPT) and 9-aminocamptothecin (ACPT) from poly (HCPT/1a) and poly(ACPT/1a), respectively, with constant UV exposure (+UV) or without UV treatment (−UV), and b) pulsatile release of HCPT and ACPT from poly(HCPT/1a) and poly(ACPT/1a), respectively, in response to periodic (every 60 min) exposure to UV for a duration of 1 min.

Poly(HCPT/1a) or poly(ACPT/1a) (0.2 mg/mL) in DMF/$H_2O$ (9:1, v/v) in a quartz cuvette was placed inside a photoreactor and irradiated for a specified period of time. The solution was centrifuged at 15,000 rpm for 15 min and the upper layer of the solution was used for HPLC analysis. See FIG. 6a for continuous exposure and FIG. 6b for pulsatile exposure.

Example 21

Procedure for the $H_2O_2$-Mediated Release of 9-Aminocamptothecin from Poly(ACPT/1d)

Poly(ACPT/1d) in DMF/$H_2O$ (9:1, v/v) (0.2 mg/mL) was stirred with $H_2O_2$ (calc. 80 mM) for a specified period of time. An $FeCl_3$ aqueous solution (10 mM, 10 µL) was added to quench the excess $H_2O_2$. After 5 min, the solution was centrifuged at 15,000 rpm for 15 min and the upper layer of the solution was used for HPLC analysis.

Example 22

General Procedure for the Photolysis of Polymers and HPLC Test

Figure 7:
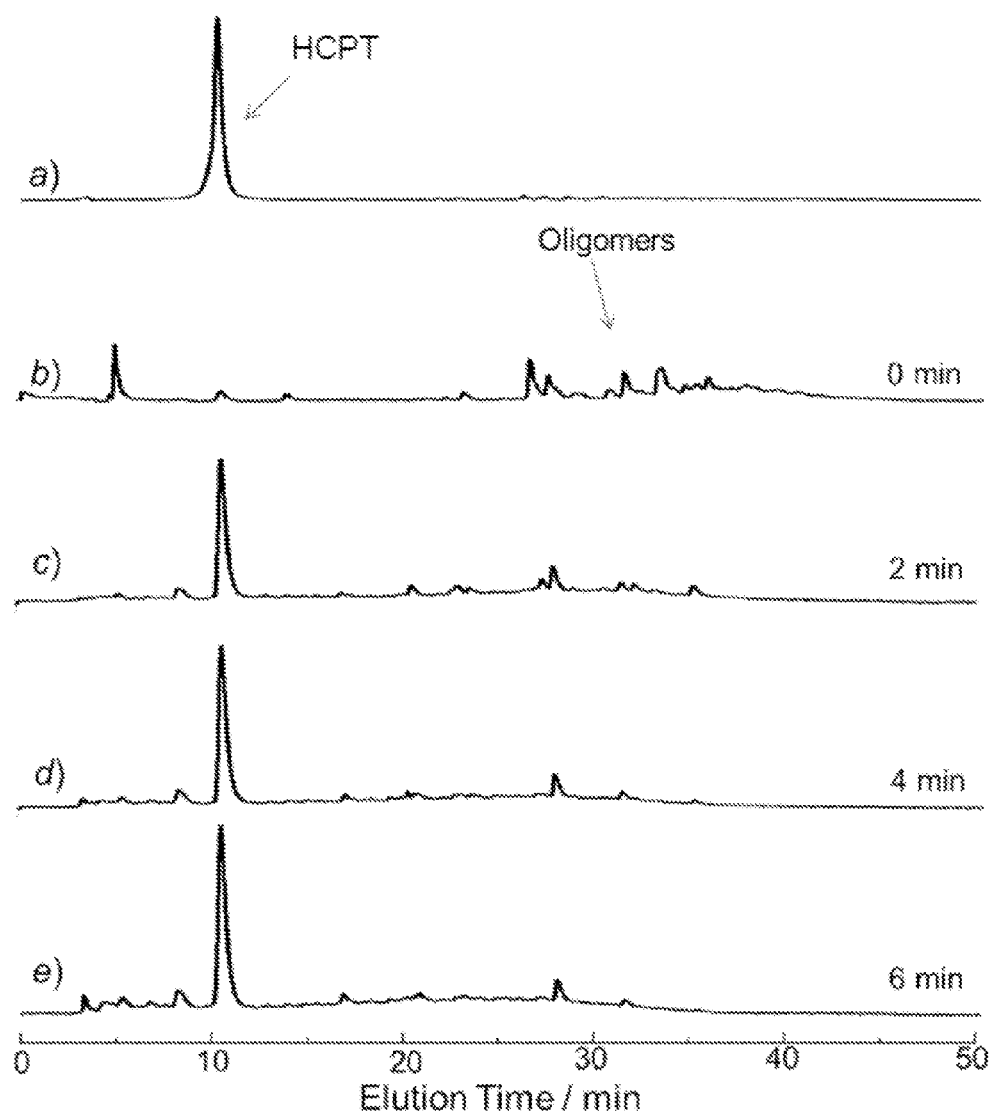
FIG. 7 shows HPLC curves of (a) 10-hydroxycamptothecin (HCPT) before treatment; (b) poly(HCPT/1a) before treatment; and (c-e) poly(HCPT/1a) after UV treatment (10 mg/mL in DMF solution, exposure in 50 mW/cm$^2$).

A quartz cuvette a solution of poly(HCPT/1a) (0.2 mg/mL in 9:1 DMF/$H_2O$) was placed in a photoreactor and irradiated for the specified periods of time. The solutions were centrifuged at 15,000 rpm for 15 min and the resulting suspensions were analyzed by HPLC. See FIG. 7.

Example 23

Cytotoxicity of Poly(HPCT/1a) Before and after UV Treatment

Figure 8:
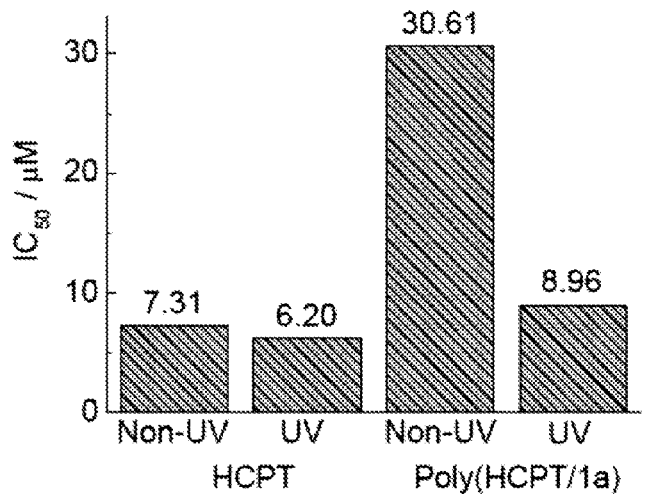
FIG. 8 shows a MTT assay for the analysis of cytotoxicity of 10-hydroxycamptothecin (HCPT) and poly(HCPT/1a) before and after UV treatment (360 nm UV, exposure for 20 min in 50 mW/cm$^2$) in HeLa cells.
Figure 9:
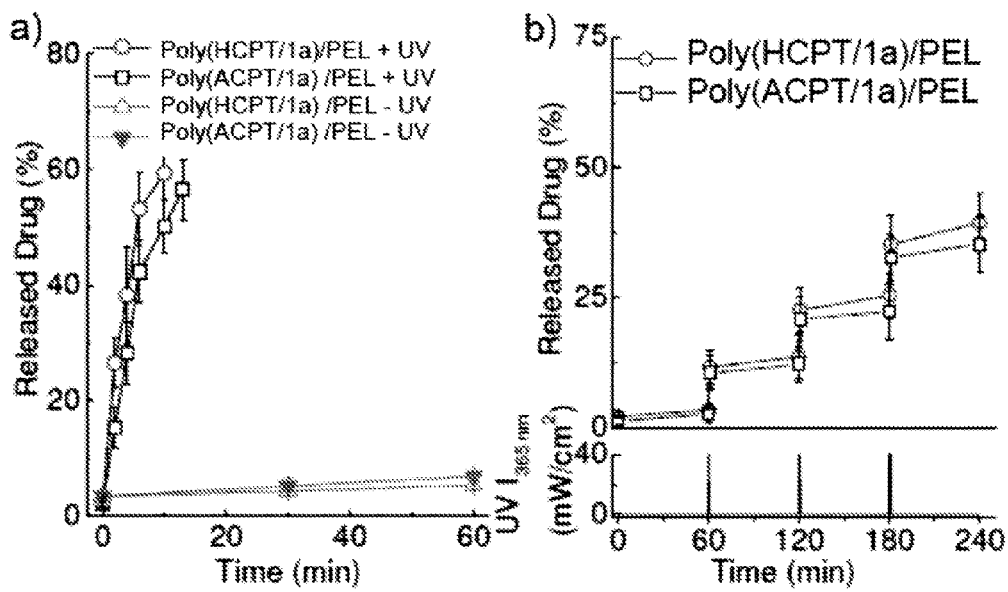
FIG. 9 shows (a) release of 10-hydroxycamptothecin (HCPT) and 9-aminocamptothecin (ACPT) from poly (HCPT/1a)/PEL and poly(ACPT/1a)/PEL nanoparticles, respectively, with constant UV exposure (+UV) or without UV treatment (−UV), and (b) pulsatile release of HCPT and ACPT from poly(HCPT/1a)/PEL and poly(ACPT/1a)/PEL nanoparticles, respectively, in response to periodic (every 60 min) exposure to UV for a duration of 1 min.

The cytotoxicity of 10-hydroxycamptothecin (HCPT) and poly(HCPT/1a) before and after UV irradiation and was evaluated in HeLa cells using the MTT assay. The polymer poly(HCPT/1a) was found to have low cytotoxicity without UV treatment, $IC_{50}$ was about 30.61 µM. After UV treatment (360 nm UV, exposure for 20 min in 50 mW/cm²), poly(HCPT/1a) showed a cytotoxicity ($IC_{50}$~8.96 µM) comparable with 10-hydroxycamptothecin (HCPT) ($IC_{50}$~6.20-7.32 µM with or without UV treatment). See FIG. 8.

Example 24

General Procedure for the Preparation of Nanoparticles from Camptothecin Containing Polymers and UV-Mediated Release of Camptothecin from the Nanoparticles Poly(HCPT/1a) or poly(ACPT/1a) (3 mg) and PEG-PLGA (3 mg) were dissolved in 1 mL DMF, and the solution was added to a vigorously stirred solution of PBS (20 mL, pH 7.4) containing. The mixture was stirred at 1000 rpm for 10 min to form poly(CPT/1a)/PEL or poly(ACPT/1a)/PEL nanoparticles (NPs). The NP suspension was stirred at 1,000 rpm for 10 min, transferred to a quartz cuvette, and then treated with UV for a specified period of time. The solution was centrifuged at 15,000 rpm for 15 min and the upper layer of the solution was used for HPLC analysis. See FIG. 8a for continuous exposure and FIG. 8b for pulsatile exposure.

What is claimed is:
1. A polymer comprising repeating units of Formula I:

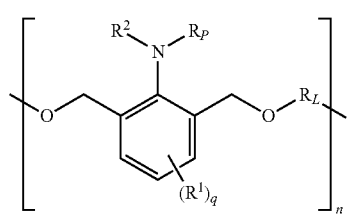

wherein
$R_P$ is a nitrogen protecting group;
each $R^1$ is independently hydrogen, hydroxyalkyl, alkyl, alkoxy, or halogen,
q is 1, 2, or 3;

$R_L$ is a group of formula A or formula B:

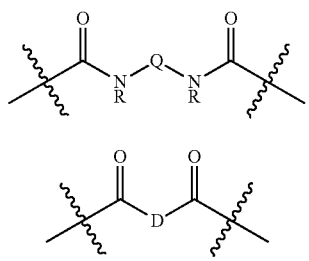

where
- Q and D are alkyl, cycloalkyl, alkenyl, cycloalkenyl, heterocyclyl, heteroalkyl, or heteroaryl, each of which is optionally substituted with one or more of alkyl, alkoxy, nitro, amino, aminoalkyl, cycloalkyl, oxo, imino, or halogen; and
- R is H or alkyl;
- $R^2$ is hydrogen, alkyl, alkenyl, alkyl-alkoxy, aryl, or arylalkyl; and n is from 2 to about 100,000.

2. A polymer according to claim 1, where each $R_P$ is independently —X—Y—Z, where
- X is —CO—, —CO$_2$—, —SO$_2$—, or —C(O)NR"—, where R" is H, alkyl, cycloalkyl, aryl or arylalkyl;
- Y is —CH$_2$—, —CH$_2$CH$_2$—, or a bond; and
- Z is aryl, alkyl, cycloalkyl, alkenyl, cycloalkenyl, heterocyclic, C(O)alkyl, alkyl-disulfide, or $NR^{23}R^{24}$, each of which is optionally substituted with one or more of aryl, alkyl, alkoxy, nitro, amino, aminoalkyl, cycloalkyl, oxo, imino, or halogen.

3. A polymer according to claim 1, in the form of an oligomer, dendrimer, cross-linked network, strand, film, fiber, resin, adhesive, coating, hydrogel, organogel or particle.

4. A method for making a polymer of claim 1, comprising: mixing a compound of Formula II:

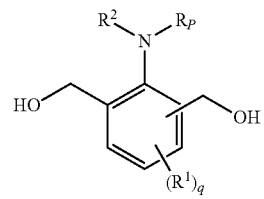

where
- $R^2$ is hydrogen, alkyl, alkenyl, alkyl-alkoxy, aryl, or arylalkyl;
- q is 1, 2, or 3;
- each $R^1$ is independently hydrogen, —CH$_2$OH, alkyl, aryl, alkoxy, arylalkyl, or halogen; provided that no more than one of $R^1$ is —CH$_2$OH, and when $R^1$ is —CH$_2$OH it is at the para position and/or remaining ortho position relative to N;

with one or more linking agents; and (b) isolating a polymer of Formula I according to claim 1.

5. A mixture comprising a polymer of claim 1 and one or more substances.

6. A method for release of the substance from the mixture of claim 5 comprising subjecting the mixture to depolymerization conditions.

7. A method for preparing the mixture of claim 6 comprising blending a polymer of claim 1 with a substance.

* * * * *